(12) United States Patent
Zaveri et al.

(10) Patent No.: US 7,109,236 B2
(45) Date of Patent: Sep. 19, 2006

(54) ANALOGS OF GREEN TEA POLYPHENOLS AS CHEMOTHERAPEUTIC AND CHEMOPREVENTIVE AGENTS

(75) Inventors: Nurulain Zaveri, San Jose, CA (US); Wan-Ru Chao, Sunnyvale, CA (US); Ahlem Bensari, Edinburgh (GB)

(73) Assignee: SRI International, Menlo Park, CA (US)

( * ) Notice: Subject to any disclaimer, the term of this patent is extended or adjusted under 35 U.S.C. 154(b) by 137 days.

(21) Appl. No.: 10/731,690

(22) Filed: Dec. 8, 2003

(65) Prior Publication Data

US 2004/0192723 A1 Sep. 30, 2004

Related U.S. Application Data

(63) Continuation-in-part of application No. 10/313,968, filed on Dec. 6, 2002.

(51) Int. Cl.
*C07D 311/02* (2006.01)
*A61K 31/352* (2006.01)

(52) U.S. Cl. .............. 514/456; 514/460; 549/396; 549/399; 549/404

(58) Field of Classification Search ............... 549/399, 549/404, 396; 514/456, 460
See application file for complete search history.

(56) References Cited

U.S. PATENT DOCUMENTS

| | | | |
|---|---|---|---|
| 4,237,162 A | 12/1980 | Kabbe et al. | |
| 4,617,296 A * | 10/1986 | Albert et al. | ............... 514/100 |
| 6,410,061 B1 | 6/2002 | Morré | |
| 2002/0151582 A1 | 10/2002 | Dou et al. | |

FOREIGN PATENT DOCUMENTS

| | | |
|---|---|---|
| JP | 2001-253879 | 9/2001 |
| WO | WO 99/22728 | 5/1999 |

OTHER PUBLICATIONS

Bam et al, Phytochemistry, vol. 39, No. 1, pp. 283-287, 1990.*
Hirose et al. (1997), "Effects of Greent Tea Catechins on the Progression or Late Promotion Stage of Mammary Gland Carcinogenesis in Female Sprague-Dawley Rats Pretreated with 7,12-Dimethylbenz(a)Anthracene," *Cancer Letters* 112: 141-147.
Li et al. (2000), "Enantioselective Synthesis of Epigallocatechin-3-Gallate (EGCG), the Active Polyphenol Component from Green Tea," *Organic Letters* 3(5):739-741.
Mukhtar et al. (1999), "Green Tea in Chemoprevention of Cancer," *Toxicoligical Science* 52(Supplement):111-117.
Zaveri (2001), "Synthesis of a 3,4,5-Trimethoxybenzoyl Ester Analogue of Epigallocatechin-3-Gallate (EGCG: A Potential Route to the Natural Product Green Tea Catechin, EGCG," *Organic Letters* 3(6):843-846.
Derwent database WPI, AN 202-307970, XP-002284951, English abstract for JP 2001-253879.
Hashimoto et al. (1996), "Evaluation of Tea Polyphenols as Anti-HIV Agents," *Bioorganic & Medicinal Chemistry Letters* 6(6):695-700.
Uesato et al. (2000), "Antitumor Promoting Activities of 3-O-Acyl-(-)-Epigallocatechins," *Bioorganic & Medicinal Chemistry Letters* 10:1673-1675.
Chemical Abstracts Service database CAPLUS, AN 1969:36948, DN 70:36948, RN:802-38-0, Clark-Lewis (1968), "Flavan Derivatives, XXV. Mass Spectra of 3-Hydroxyflavanones, Flavan -3-ols, and Flavan-3,4-diols," *Australian Journal of Chemistry* 21(12):3025-3054 (abstract only).
Lee al. (1992), "Flavan-3-ol Gallates and Proanthocyanidins from Pithecellobium Lobatum," *Phytochemistry* 31(6):2117-2120.
Weinges (1964), "The Occurrence of Catechins in Fruits," *Phytochemistry* 3:263-266.
Zhu et al. (2001), "Study of Tea Polyphenol as a Reversal Agent for Carcinoma Cell Lines' Multidrug Resistance (Study of TP as a MDR Reversal Agent," *Nuclear Medicine and Biology* 28:735-740.

* cited by examiner

*Primary Examiner*—Zinna N. Davis
(74) *Attorney, Agent, or Firm*—Mintz, Levin, Cohn, Ferris, Glovsky and Popeo, P.C.

(57) ABSTRACT

Novel compounds useful as chemotherapeutic and chemopreventive agents are provided. The compounds are analogs of polyphenol catechins that occur in green tea, such as epigallocatichin-3-gallate (EGCG), and have the structure of formula (I)

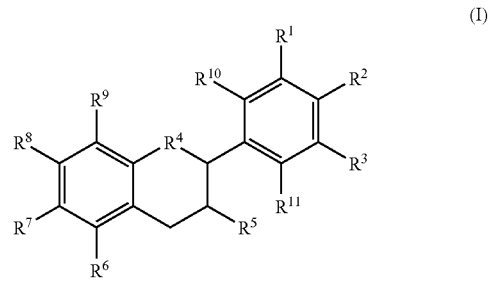

(I)

wherein $R^1$ through $R^{11}$ are defined herein. Preferred $R^4$ moieties are selected from O, S, NH and $CH_2$, and in exemplary compounds, $R^4$ is O and $R^5$ is a tri-substituted aroyloxy substituent, such as a 3,4,5-substituted benzoyloxy group. Pharmaceutical compositions are provided as well, as are methods of chemotherapy and chemoprevention.

28 Claims, 6 Drawing Sheets

Scheme 1

Scheme 2

Scheme 3

Scheme 4

ANALOGS OF GREEN TEA POLYPHENOLS AS CHEMOTHERAPEUTIC AND CHEMOPREVENTIVE AGENTS

CROSS-REFERENCE TO RELATED APPLICATIONS

This application is a continuation-in-part of application Ser. No. 10/313,968, filed Dec. 6, 2002, which is incorporated by reference in its entirety.

TECHNICAL FIELD

This invention relates generally to analogs of polyphenol catechins that occur in green tea. More particularly, the invention pertains to novel analogs of the catechin, (−)-epigallocatechin-3-gallate (EGCG), and to their use as chemotherapeutic and chemopreventive agents.

BACKGROUND

Cancer is the second leading cause of death in the United States, exceeded only by heart disease. Current pharmacological treatments for cancer utilize a toxic dose of a compound that is administered in a precise dosing range to preferentially destroy the cancerous cells (chemotherapy), and minimize damage to healthy tissue. Despite efforts to focus the toxic effects on the cancerous tissues, severe or even life-threatening adverse effects may occur, such as serious disorders of the blood, gastrointestinal tract, liver, kidneys, and other organs. Most current anticancer drugs thus have a narrow therapeutic window: the range between the therapeutic dose and the maximum tolerated dose is very small. Due to this toxicity, as well as the fact that most anticancer drugs are administered intravenously, nearly all cancer chemotherapy must be administered in a hospital or clinic. An additional problem with most current cancer chemotherapy is that cancers frequently develop resistance to the drugs, so that recurrence of disease is common.

It is a goal of cancer researchers to discover efficacious anticancer agents while avoiding the adverse effects of chemotherapy treatments. Epidemiology offers some clues in this regard, and has led to the discovery of safe anticancer agents. By examining the practices of cultures exhibiting a lower incidence of cancer and investigating the possible sources of the decreased incidence of disease, researchers may be able to discover that the food or drink consumed by the people of that culture contains compounds that have anticancer properties. These dietary compounds possessing anticancer properties can then be modified to enhance their anticancer effects while retaining their safety. Of particular interest in this regard are certain polyphenols that occur in green tea.

Specifically, compounds such as the catechins, (−)-epigallocatechin-3-gallate (EGCG), (−)-epigallocatechin (EGC), (−)-epicatechin-3-gallate (ECG), and (−)-epicatechin (EC) have been implicated in cancer chemoprevention. Both EGCG and EGC exhibit substantial anticancer activity (EGCG is particularly potent), with ECG and EC somewhat less active.

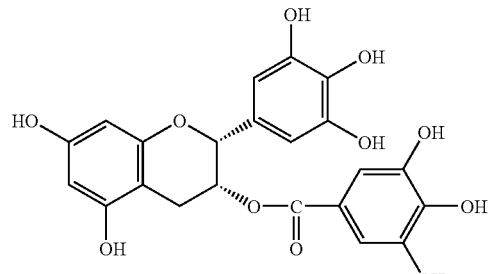

(−)-EPIGALLOCATECHIN-3-GALLATE (EGCG)

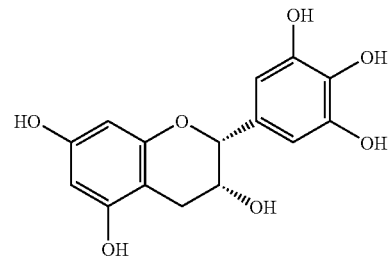

(−)-EPIGALLOCATECHIN (EGC)

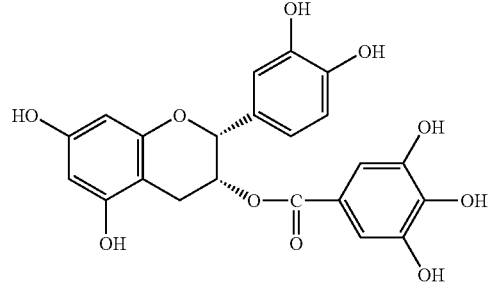

(−)-EPICATECHIN-3-GALLATE (ECG)

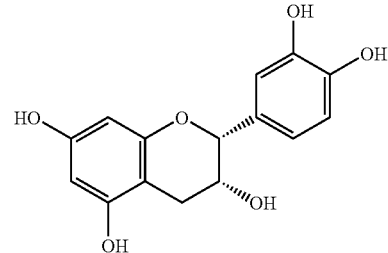

(−)-EPICATECHIN (EC)

Researchers studying these naturally occurring polyphenols have determined that EGCG is not only the most abundant of the above catechins, but also the most potent chemopreventive component in green tea. A large number of in vitro and in vivo studies have shown EGCG to possess a wide variety of anticancer activities. In animal studies, orally administered EGCG and related green tea polyphenols have shown efficacy in preventing and treating cancers of the lung, breast, liver, skin, esophagus, stomach, duodenum, pancreas, and colon (Hirosi et al. (1997) *Cancer Lett.* 112:141–147). As an antioxidant, EGCG exerts antimutagenic and chemoprotective effects through neutralization of free radicals, protection of DNA from strand breaks and other damage caused by reactive oxygen species (Anderson et al. (2001) *Carcinogenesis* 22:1189–1193), and inhibition of oxidation of some carcinogenic substrates of human cytochrome P450 (Muto et al. (2001) *Mutat. Res.* 479: 197–202). In general, EGCG inhibits the metabolic activation of procarcinogens by cytochrome P450, which represents a significant chemoprotective activity against carcinogenesis (ibid).

Another proposed anticancer activity of EGCG involves the induction of apoptosis. One mechanism of apoptosis appears to be binding of EGCG to Fas on the cell surface, which triggers Fas-mediated apoptosis (Hayakawa et al. (2001) *Biochem. Biophys. Res. Commun.* 285:1102–1106). Other researchers have suggested that normal cells are not affected by the apoptotic effects of green tea polyphenols because EGCG and other constituents of green tea cause the induction of p57, which acts to inhibit apoptosis in untransformed cells (Hsu et al. (2001) *Anticancer Res.* 21 (6A): 3743–3748).

Other anticancer mechanisms include, without limitation: inhibition of topoisomerases I and II (Suzuki et al. (2001) *Biol. Pharm. Bull.* 24:1088–1090); inhibition of nuclear factor kappa-B (NFκB), possibly through inhibition of the IκB kinase complex (Yang et al. (2001) *Mol. Pharmacol.* 60:528–533), which results in the suppression of NO synthesis and subsequent generation of carcinogenic nitrites; scavenging of carcinogenic nitrites (Pannala et al. (1997) *Biochem. Biophys. Res. Commun.* 232:164–168); inhibition of matrix metalloproteinases involved in tumor metastasis (Isemura et al. (2000) *Biofactors* 13:81–85; Demeule et al. (2000), *Biochim. Biophys. Acta* 1478:51–60); inhibition of the androgen receptor in prostate cancer (Ren et al. (2000) *Oncogene* 19:1924–1932); inhibition of cellular hyperproliferation induced by overexpression of epidermal growth factor receptor (Liang et al. (1997) *J. Cell Biochem.* 67:55–65); and inhibition of angiogenesis, at least in part by suppressing the induction of vascular endothelial growth factor (VEGF) (Jung et al. (2001) *Br. J. Cancer* 84:844–850).

EGCG can be obtained as the natural product (see, e.g., U.S. Pat. No. 6,210,679 to Bailey et al.) or chemically synthesized using an enantioselective synthesis recently developed at SRI International (Menlo Park, Calif.); see Zaveri (2001) *Organic Letters* 3(6):843–846. However, EGCG per se is not a viable candidate for use as a therapeutic agent because it is only minimally bioavailable when administered orally, and in addition, EGCG is extensively conjugated by action of the liver. Because of the poor absorption when given orally, one would have to drink at least 8–10 cups of green tea a day to gain its chemopreventive benefit (EGCG is present in green tea at a concentration of about 200 mg per brewed cup; see Mukhtar et al. (1999) *Toxicol. Sci.* 52 (suppl.):111 –117). Furthermore, green tea contains 70 mg of caffeine per cup, so drinking enough for chemoprevention would result in caffeine-related side effects. These are being observed in the ongoing clinical trials of green tea.

Several researchers have attempted to synthesize analogs of EGCG that overcome the aforementioned limitations inherent in EGCG itself For example, it is not yet known which of the enantiomers of EGCG is responsible for the anticancer activity of this compound. An enantioselective synthesis of EGCG was devised involving synthesizing the three aromatic fragments separately, and then assembling them in a stereoselective fashion (Li and Chan (2001) *Organic Letters* 3(5):739–741). These authors however did not report any results regarding the relative efficacy of either enantiomer. Zaveri (2001), supra, describes synthesis of a 3,4,5-trimethoxybenzoyl ester analogue of EGCG and the 2α,3β enantiomer thereof. Although both compounds described by Zaveri were found to inhibit the growth of breast cancer cell lines in vitro, the potency of these compounds was somewhat less than that of EGCG itself.

Accordingly, there is a need for synthetic strategies for generating analogs of EGCG and other green tea polyphenols, in order to optimize the chemopreventive and chemotherapeutic effects of these compounds. The present invention is the result of extensive, systematic research to design novel flavanoids related to EGCG, but optimized to enhance their anticancer activity and retain a low toxicity.

SUMMARY OF THE INVENTION

The present invention is directed to novel EGCG analogs that, like EGCG per se, are highly effective anti-cancer agents, but which in contrast to EGCG possess excellent oral bioavailability. The novel compounds provide a number of advantages relative to compounds that are known or currently under consideration as anticancer agents. For example, the present compounds have a very broad therapeutic window, in turn meaning that no toxicity will be seen even at high doses. In addition, the compounds do not give rise to the numerous and debilitating side effects that are associated with many drugs. From a safety standpoint, then, the novel compounds are optimal. Furthermore, the present compounds have simple molecular structures, and may be readily synthesized using straightforward synthetic techniques. Pharmaceutical compositions formulated with the novel compounds are stable and readily delivered, providing excellent bioavailability.

The invention thus provides novel compounds that are useful as chemotherapeutic and chemopreventive agents. The novel compounds are flavanoids that are structurally related to EGCG and other polyphenols found in green tea.

In one embodiment, a therapeutic compound is provided having the structure (I)

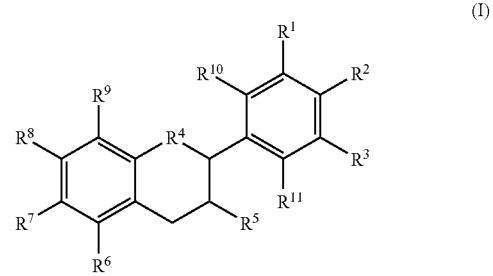

wherein:

$R^1$, $R^2$, and $R^3$ are selected from the group consisting of hydrogen, hydroxyl, alkyl, halo, sulthydryl, alkoxy, and aryloxy, and further wherein either $R^1$ and $R^2$, or $R^2$ and $R^3$, can be linked to form a cyclic group;

$R^4$ is selected from O, S, $NR^x$, and $CR^yR^z$, wherein $R^x$, $R^y$, and $R^z$ are hydrogen or alkyl;

$R^5$ is selected from the group consisting of acyloxy (including aroyloxy), sulthydryl, and $N(R^x)$ wherein the $R^x$ may be the same or different and are as defined previously;

$R^6$, $R^7$, $R^8$, and $R^9$ are independently selected from the group consisting of hydrogen, hydroxyl, alkyl, alkoxy, and aryloxy, providing that either $R^6$ and $R^7$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{10}$ and $R^{11}$ are independently selected from the group consisting of hydrogen, hydroxyl, alkyl, alkoxy, and halo, with the proviso that when (a) $R^7$, $R^9$, $R^{10}$, and $R^{11}$ are hydrogen, (b) $R^1$, $R^2$, $R^6$, and $R^8$ are hydroxyl, (c) $R^3$ is hydrogen or hydroxyl, and (d) $R^4$ is O, then (e) $R^5$ is other than 3,4,5-trihydroxybenzoyloxy or 3,4,5-trimethoxybenzoyloxy.

In another embodiment, a compound is provided having the structure of formula (II)

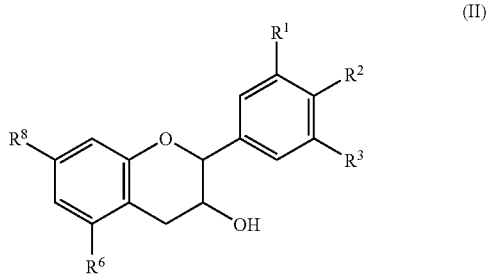

(II)

wherein:

$R^1$, $R^2$, and $R^3$ are selected from the group consisting of hydroxyl, alkyl, halo, sulfhydryl, alkoxy, and aryloxy, and further wherein either $R^1$ and $R^2$, or $R^2$ and $R^3$, can be linked to form a cyclic group;

$R^6$ and $R^8$ are selected from the group consisting of hydrogen, alkyl, alkoxy, and aryloxy, wherein $R^1$, $R^2$, $R^3$, $R^6$ and $R^8$ are not all the same.

In yet another embodiment, EGCG analogs are provided wherein the analogs contain at least one modification relative to EGCG per se which results in an $IC_{50}$ of less than 60 when the analogs are evaluated for their ability to inhibit growth in a breast cancer cell line using the MTT assay according to the protocol provided by the manufacturer (Promega, Madison, Wis.).

The methods used to synthesize the compounds are straightforward, avoid the use of extreme reaction conditions and toxic solvents, and provide the desired products in high yield.

In an additional embodiment, the invention encompasses pharmaceutical compositions containing a novel compound as provided herein in combination with a pharmaceutically acceptable carrier. Preferably, although not necessarily, such compositions are oral dosage forms and thus contain a carrier suitable for oral drug administration.

In a further embodiment, the invention is directed to a method for treating an individual suffering from cancer, comprising administering to the individual a therapeutically effective amount of a novel compound as provided herein. In addition to their general utility as chemotherapeutic agents, the compounds are also useful in chemoprevention. Therefore, the invention additionally pertains to a method for preventing cancer, by administering a therapeutically effective amount of a compound of the invention to a patient. Generally, in chemoprevention, the patient will have been identified as being at an elevated risk of developing cancer. Such patients include, for example, those with a family history of cancer or a particular type of cancer, as well as those who have undergone genetic analysis and thereby determined to be genetically predisposed to develop cancer or a particular type of cancer.

DETAILED DESCRIPTION OF THE PREFERRED EMBODIMENTS

Figure 1:
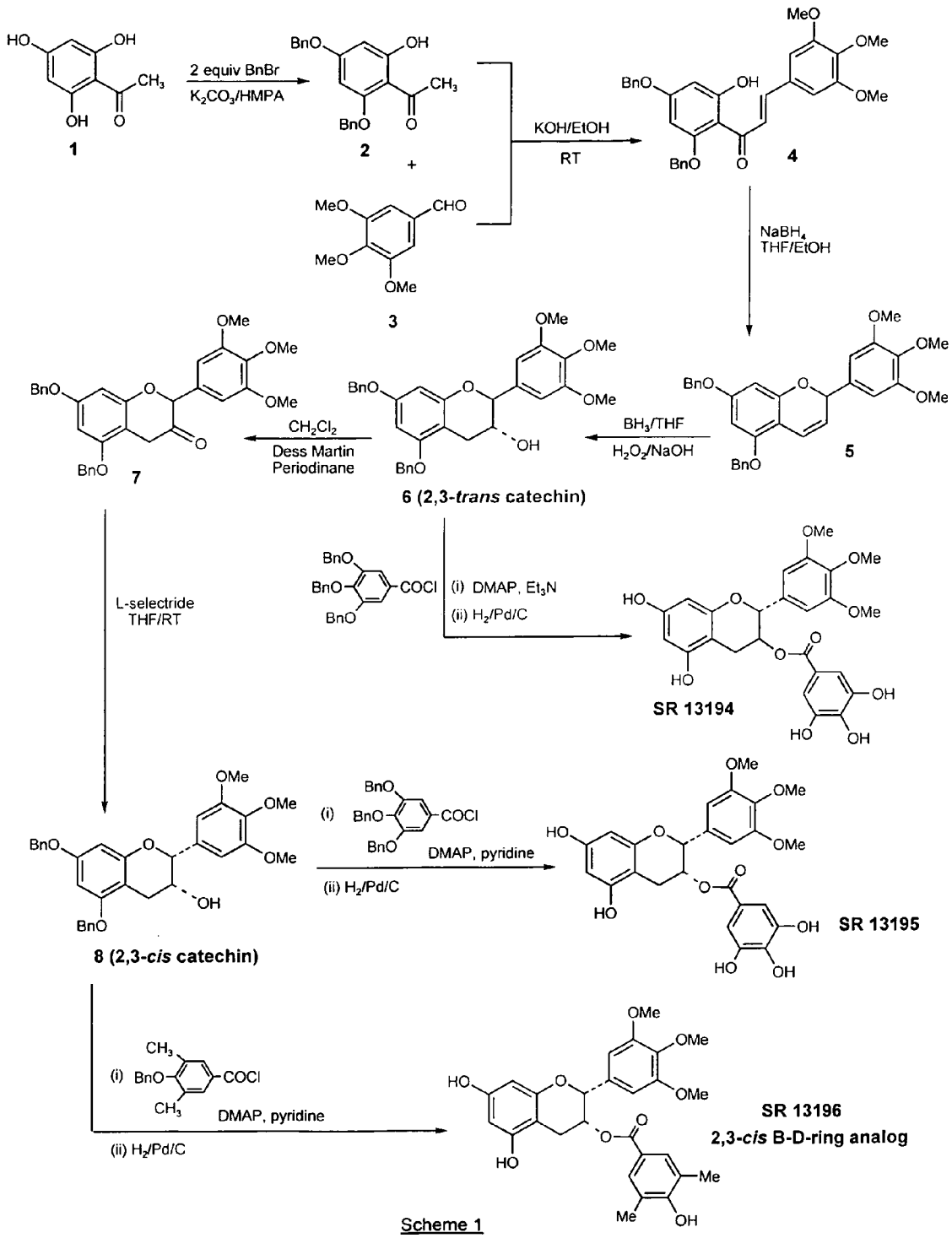
FIG. 1 schematically illustrates the stepwise synthesis of three compounds of the invention, SR 13194, SR 13195, and SR 13196, as described in Examples 1 through 3, respectively.
Figure 2:
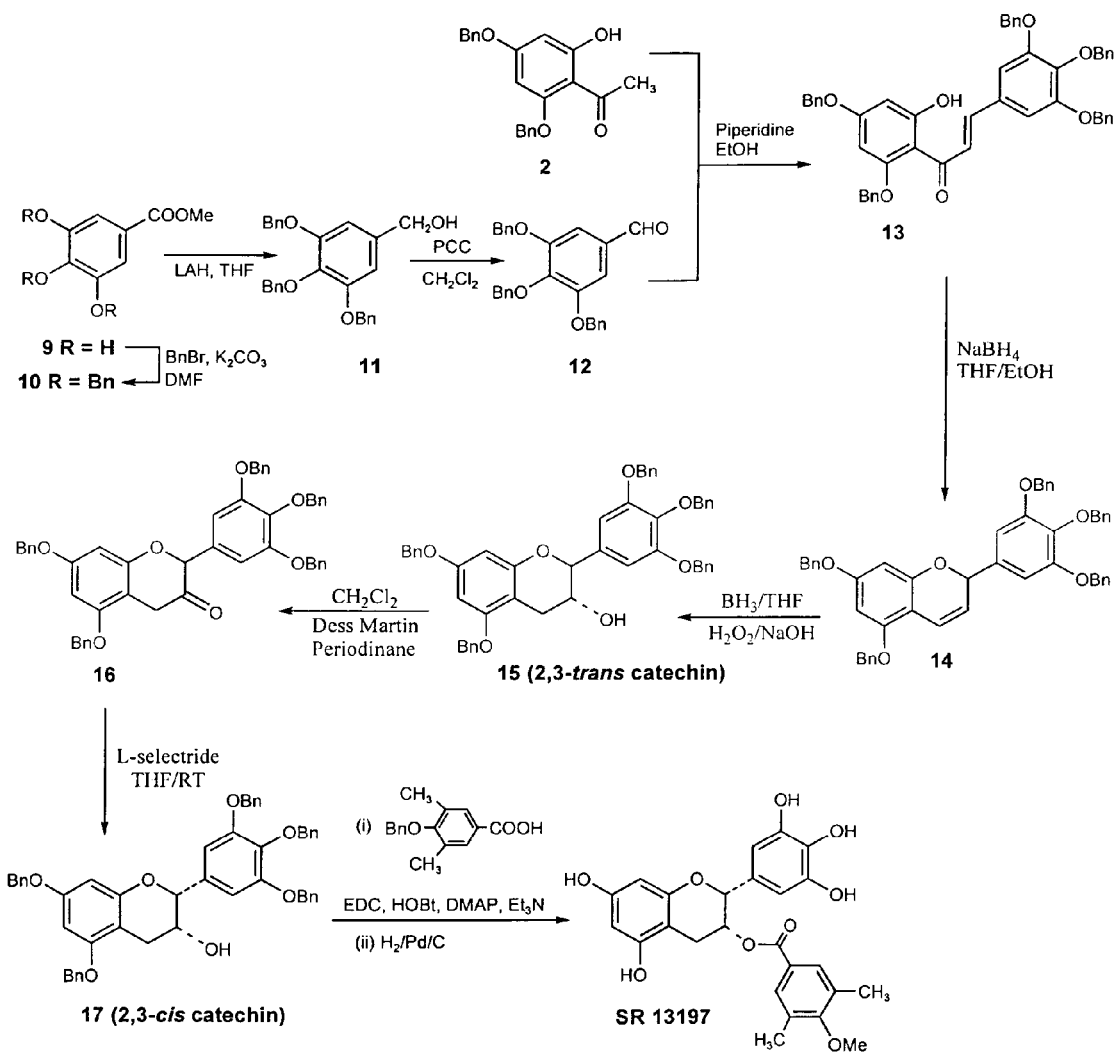
FIG. 2 schematically illustrates the stepwise synthesis of an additional compound of the invention, SR 13197, as described in Example 4.
Figure 3:
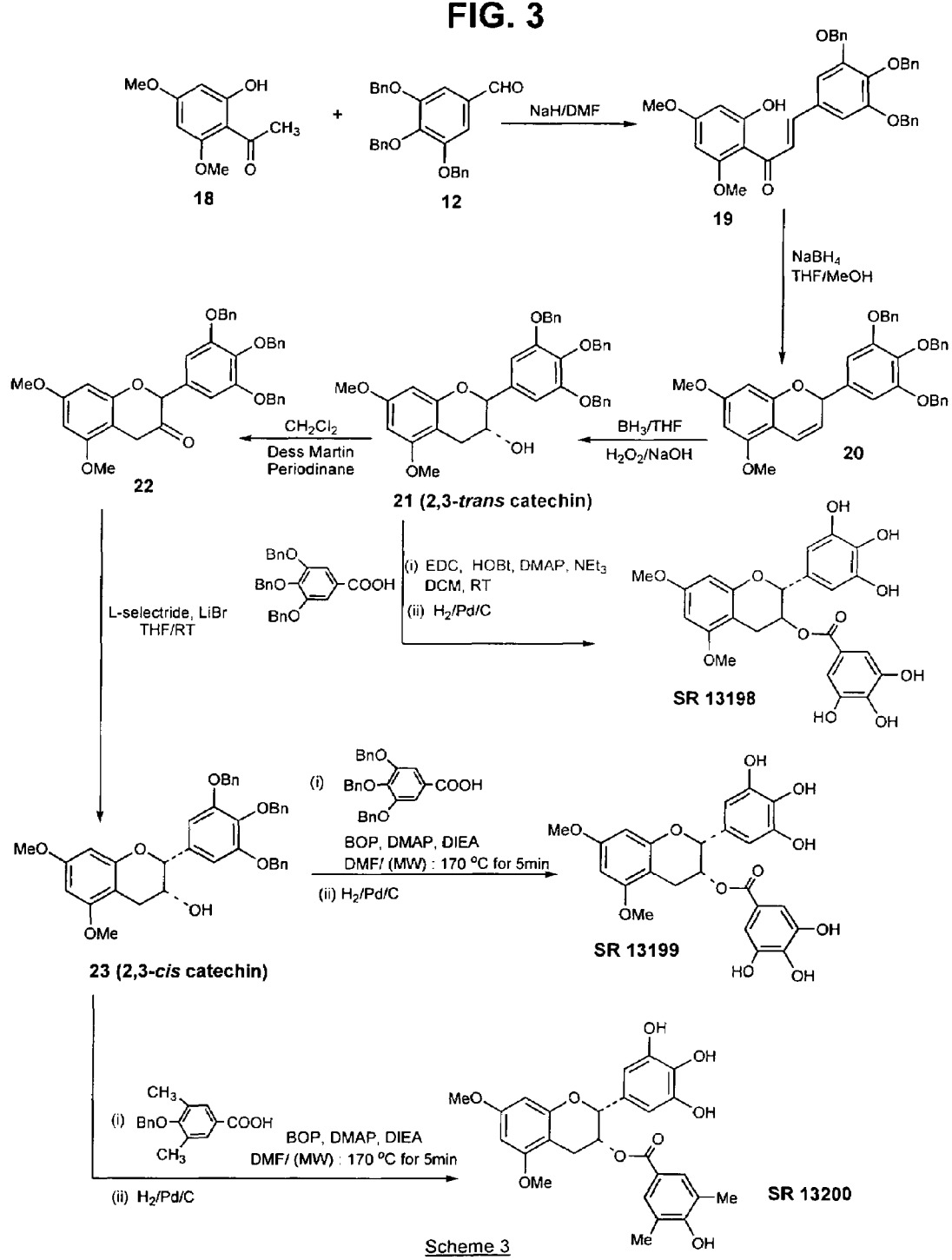
FIG. 3 schematically illustrates the stepwise synthesis of three additional compounds of the invention, SR 13198, SR 13199, and SR 13200, as described in Examples 5 through 7, respectively.
Figure 4:
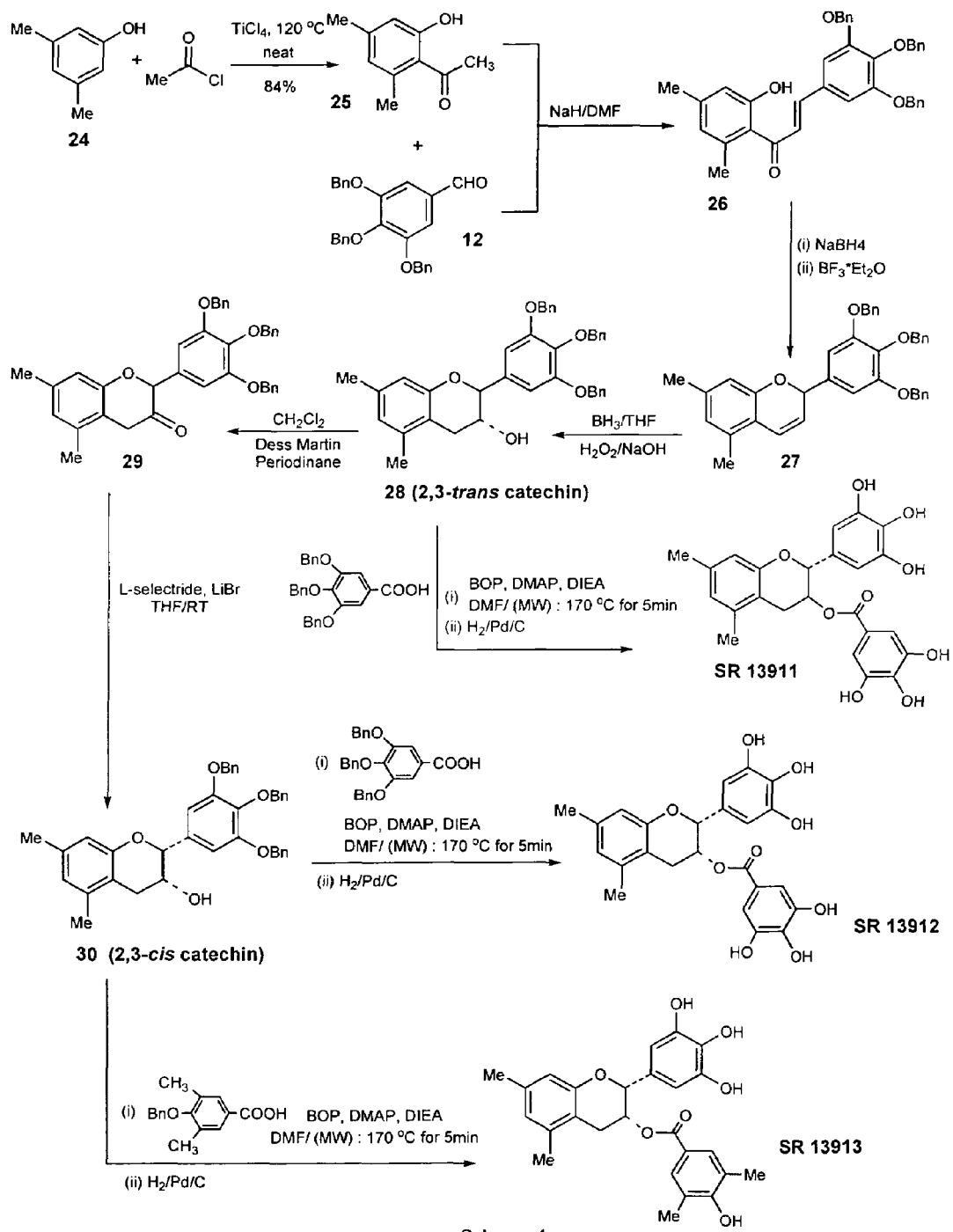
FIG. 4 schematically illustrates the stepwise synthesis of three additional compounds of the invention, SR 13911, SR 13912, and SR 13913, as described in Examples 8 through 10, respectively.

I. Definitions and Nomenclature:

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

In this specification and in the claims that follow, reference will be made to a number of terms, which shall be defined to have the following meanings:

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of I to 6 carbon atoms. Preferred substituents identified as "$C_1$–$C_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$–$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "aroyl" (e.g., benzoyl) refers to a substituent having the structure —(CO)-aryl (e.g., —(CO)-phenyl), and the term "aroyloxy" (e.g., benzoyloxy) refers to a substituent having the structure —O—(CO)-aryl (e.g., —O—(CO)-phenyl).

The term "aralkyl" refers to an alkyl group with an aryl substituent, wherein "aryl" and "alkyl" are as defined above. Preferred aralkyl groups contain 5 to 20 carbon atoms, and particularly preferred aralkyl groups contain 5 to 12 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "aralkyloxy" refers to an aralkyl group bound through a single, terminal ether linkage. As above, an "aralkyloxy" group may be represented as —O-Alk(Ar) wherein "Alk" is an alkyl group and "Ar" is an aryl substituent. Preferred aralkyloxy groups contain 5 to 20 carbon atoms, and particularly preferred aralkyloxy groups contain 5 to 12 carbon atoms. Aralkyloxy substituents include, for example, benzyloxy, 2-phenoxy-ethyl, 3-phenoxy-propyl, 2-phenoxy-propyl, 2-methyl-3-phenoxypropyl, 2-ethyl-3-phenoxypropyl, 4-phenoxy-butyl, 3-phenoxy-butyl, 2-methyl-4-phenoxybutyl, 4-phenoxycyclohexyl, 4-benzyloxycyclohexyl, 4-phenoxy-cyclohexylmethyl, 2-(4-phenoxy-cyclohexyl)-ethyl, and the like.

The term "cyclic" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic"

refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$–$C_{24}$ alkoxy, $C_2$–$C_{24}$alkenyloxy, $C_2$–$C_{24}$ alkynyloxy, $C_5$–$C_{20}$ aryloxy, acyl (including $C_2$–$C_{24}$ alkylcarbonyl (—CO-alkyl) and $C_6$–$C_{20}$ arylcarbonyl (—CO—aryl)), acyloxy (—O-acyl), $C_2$–$C_{24}$ alkoxycarbonyl (—(CO)—O-alkyl), $C_6$–$C_{20}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{20}$ arylcarbonato (—O—(CO)—O-aryl), carboxy (—COOH), carboxylato (—COO$^-$), carbamoyl (—(CO)—NH$_2$), mono-($C_1$–$C_{24}$ alkyl)-substituted carbamoyl (—(CO)—NH($C_1$–$C_{24}$ alkyl)), di-($C_1$–$C_{24}$ alkyl)-substituted carbamoyl (—(CO)—N($C_1$–$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato —S—C≡N), azido (—N=N$^+$=N$^-$), formyl (—(CO)—H), thioformyl (—(CS)—H), amino (—NH$_2$), mono- and di-($C_1$–$C_{24}$ alkyl)-substituted amino, mono- and di-($C_5$–$C_{20}$ aryl)-substituted amino, $C_2$–$C_{24}$ alkylamido (—NH—(CO)—alkyl), $C_6$–$C_{20}$ arylamido (—NH—(CO)-aryl), imino (—CR=NH where R=hydrogen, $C_1$–$C_{24}$ alkyl, $C_5$–$C_{20}$ aryl, $C_6$–$C_{24}$ alkaryl, $C_6$–$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$–$C_{24}$ alkylsulfanyl (—S-alkyl; also termed "alkylthio"), arylsulfanyl (—S-aryl; also termed "arylthio"), $C_1$–$C_{24}$ alkylsulfinyl (—(SO)-alkyl), $C_5$–$C_{20}$ arylsulfinyl (—(SO)-aryl), $C_1$–$C_{24}$ alkylsulfonyl (—SO$_2$-alkyl), $C_5$–$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$–$C_{24}$ alkyl (preferably $C_1$–$C_{18}$ alkyl, more preferably $C_2$–$C_{12}$ alkyl, most preferably $C_1$–$C_6$ alkyl), $C_2$–$C_{24}$ alkenyl (preferably $C_2$–$C_{18}$ alkenyl, more preferably $C_2$–$C_{12}$ alkenyl, most preferably $C_2$–$C_6$ alkenyl), $C_2$–$C_{24}$ alkynyl (preferably $C_2$–$C_{18}$ alkynyl, more preferably $C_2$–$C_{12}$ alkynyl, most preferably $C_2$–$C_6$ alkynyl), $C_5$–$C_{20}$aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "an optionally present bond" as indicated by a dotted line - - - - - in the chemical formulae herein means that a bond may or may not be present.

In the molecular structures herein, the use of bold and dashed lines to denote particular conformation of groups follows the IUPAC convention. A bond indicated by a broken line indicates that the group in question is below the general plane of the molecule as drawn (the "β" configuration), and a bond indicated by a bold line indicates that the group at the position in question is above the general plane of the molecule as drawn (the "α" configuration). Single bonds that are not indicated by broken or bold lines may be in either configuration; such bonds may also be indicated by the conventional symbols ——— or ∿∿∿ .

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. For example, treatment of a patient by administration of an anti-cancer agent of the invention encompasses chemoprevention as well as chemotherapy and antiangiogenesis.

By the terms "effective amount" or "therapeutically effective amount" of a compound of the invention is meant a nontoxic but sufficient amount of the drug or agent to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

II. The Novel Compounds:

The compounds of the invention are flavanoids and analogs thereof, having the structure of formula (I)

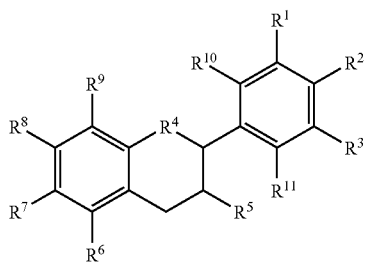

(I)

wherein the various substituents are defined as follows.

$R^1$, $R^2$, and $R^3$ are selected from: hydrogen; hydroxyl; alkyl, preferably $C_1$–$C_6$, alkyl, particularly methyl; sulfhydryl; halo; alkoxy, preferably $C_1$–$C_6$ alkoxy, such as methoxy and ethoxy, with methoxy preferred; and aryloxy, preferably $C_5$–$C_{12}$ aryloxy, with phenoxy preferred. The alkoxy and aryloxy substituents are optionally heteroatom-containing and/or may be substituted with one or more, typically one or two substituents. Of course, it will be appreciated that any substituents should not be detrimental to the therapeutic efficacy of the compound, nor should they be reactive with or otherwise interact adversely with other components of the pharmaceutical composition in which the compound is contained. Substituents include functional groups, hydrocarbyl groups, and combinations thereof as described in part (I) of this section.

In addition, either $R^1$ and $R^2$, or $R^2$ and $R^3$, can be linked to form a cyclic structure, which typically, although not necessarily, is selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents such as those enumerated above and zero to 3 heteroatoms. For example, either $R^1$ and $R^2$, or $R^2$ and $R^3$, can be joined to form a lower alkylene linkage, e.g., —(CH$_2$)$_3$— or —(CH$_2$)$_3$—, a lower alkylene linkage substituted with a substituent as described above, a lower heteroalkylene linkage, e.g., —O—CH$_2$—O—, —CH$_2$—O—CH$_2$, or —CH$_2$—NH—CH$_2$, in which case the remaining R group, i.e., $R^1$ or $R^3$, is hydroxyl, $C_1$–$C_6$ alkoxy, aryloxy, or aralkyloxy.

$R^4$ is selected from O, S, NR$^x$, and CR$^y$R$^z$, wherein R$^x$, R$^y$, and R$^z$ are hydrogen or alkyl. Preferably, R$^x$, R$^y$, and R$^z$ are hydrogen, such that $R^4$ is O, S, NH or CH$_2$. In a most preferred embodiment, $R^4$ is O.

$R^5$ is selected from the group consisting of SH, N(R$^x$)$_2$ wherein the R$^x$ may be the same or different and are selected from hydrogen, alkyl, aryl, and aralkyl, and esters of the structure —O—(CO)—R (i.e., acyloxy groups) in which R is substituted or unsubstituted alkyl, aryl, or aralkyl. In preferred such esters, R is alkyl, particularly $C_1$–$C_6$ alkyl, or substituted phenyl. Generally, such acyloxy substituents have 2 to 32 carbon atoms, preferably 6 to 32 carbon atoms.

Preferred acyloxy groups are aroyloxy groups, with exemplary such groups having the structure

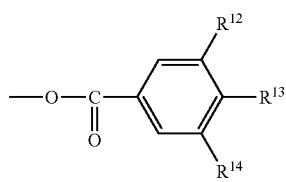

wherein $R^{12}$, $R^{13}$, and $R^{14}$ are independently selected from the group consisting of hydrogen, hydroxyl, alkyl, alkoxy, and aryloxy. Within this group, the most preferred substituents are wherein $R^{12}$, $R^{13}$, and $R^{14}$ are independently selected from the group consisting of hydroxyl, $C_1$–$C_6$ alkyl (preferably methyl), and $C_1$–$C_6$ alkoxy (preferably methoxy).

$R^6$, $R^7$, $R^8$, and $R^9$ are independently selected from the group consisting of: hydrogen; hydroxyl, alkyl, preferably $C_1$–$C_6$ alkyl, such as methyl and ethyl, with methyl preferred; alkoxy, preferably $C_1$–$C_6$ alkoxy, such as methoxy and ethoxy, with methoxy preferred; and aryloxy, preferably $C_5$–$C_{12}$ aryloxy, with phenoxy preferred. Either $R^6$ and $R^7$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms. Compounds wherein either $R^6$ and $R^7$, or $R^8$ and $R^9$, are linked to form a phenyl or heteroaromatic ring (e.g., pyridinyl, pyrimidinyl, etc.) "fused" to the first are preferred. The phenyl or heteroaromatic ring formed by linkage of $R^6$ to $R^7$, or of $R^8$ to $R^9$, may be further substituted in a similar manner to form a fused tricyclic structure such as an anthracene, phenanthrene, or benzo[h]quinoline system. Particularly preferred such compounds are α-naphthaflavanoids, wherein $R^6$ and $R^7$ are hydrogen, and $R^8$ and $R^9$ are linked to form a phenyl ring.

$R^{10}$ and $R^{11}$ are independently selected from the group consisting of hydrogen, hydroxyl, $C_1$–$C_6$ alkyl, $C_1$–$C_6$ alkoxy, and halo. Preferably, $R^{10}$ and $R^{11}$ are hydrogen.

The aforementioned substituents are defined as indicated with the proviso that the compound of formula (I) excludes the natural products EGCG, EGC, and EC, as well as the 3,4,5-trimethoxybenzoyloxy analog of EGCG, such that when (a) $R^7$, $R^9$, $R^{10}$, and $R^{11}$ are hydrogen, (b) $R^1$, $R^2$, $R^6$, and $R^8$ are hydroxyl, (c) $R^3$ is hydrogen or hydroxyl, and (d) $R^4$ is O, then (e) $R^5$ is other than 3,4,5-trihydroxybenzoyloxy or 3,4,5-trimethoxybenzoyloxy.

In compounds of formula (I), if it will be appreciated that because of the two chiral centers, four different enantiomers are possible, and the compound may be in the form of an individual enantiomer or as a racemic mixture of enantiomers. In the following representation, the chiral centers are represented with a * and the bonds with alternative configurations are indicated by ∿∿∿.

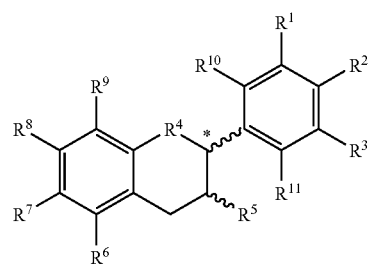

Accordingly, the four possible enantiomers are as follows:

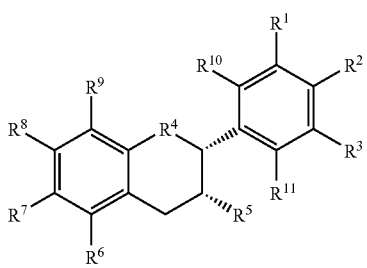

2β,3β-cis

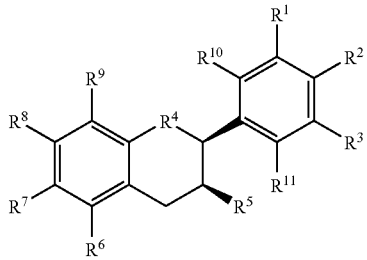

2α,3α-cis

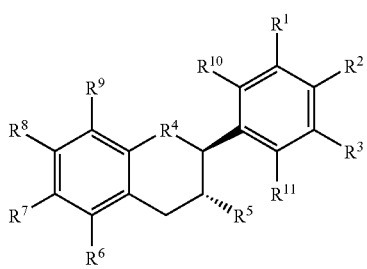

2α,3β-trans

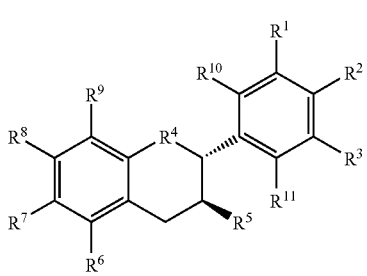

2β,3α-trans

Generally, although not necessarily, the compound of the invention will be a racemic mixture of the two trans enantiomers. Such a mixture is indicated in the molecular structures herein as follows:

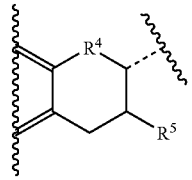

Compounds in the form of a racemic mixture of the two cis enantiomers are represented by the following structure:

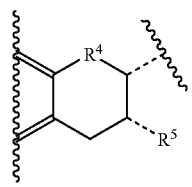

Particularly preferred compounds of formula (I) are wherein: $R^4$ is O; $R^5$ is an ester substituent R—(CO)—O— wherein R is phenyl substituted at the 3-, 4-, and 5-positions with substituents independently selected from the group consisting of hydroxyl, methyl, and methoxy; and $R^7$, $R^9$, $R^{10}$, and $R^{11}$ are hydrogen.

Accordingly, particularly preferred compounds of the invention have the structure (III)

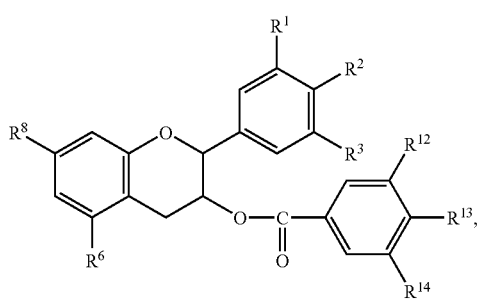

in either the cis (IVA) or trans (IVB) form

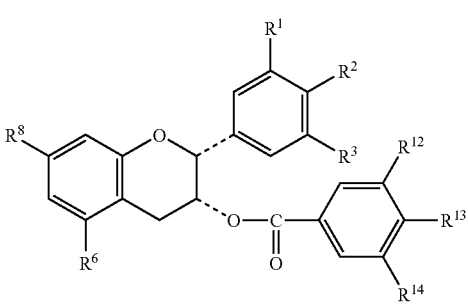

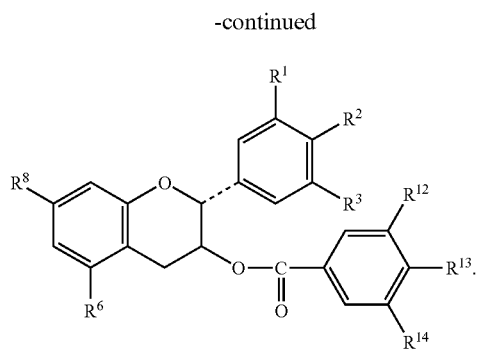
(IVB)

In a most preferred embodiment, $R^1$, $R^2$, $R^3$, $R^6$, $R^8$, $R^{12}$, $R^{13}$, and $R^{14}$ are independently selected from hydroxyl, methyl, and methoxy, with the proviso that the compound of formula (I) excludes EGCG per se, such that when (i) $R^1$, $R^2$, $R^6$, and $R^8$ are hydroxyl, and (ii) $R^3$ is hydroxyl, then (e) $R^5$ is other than 3,4,5-trihydroxybenzoyloxy or 3,4,5-trimethoxybenzoyloxy.

Specific examples of compounds of the invention include, but are not limited to, the following.

SR 13194:

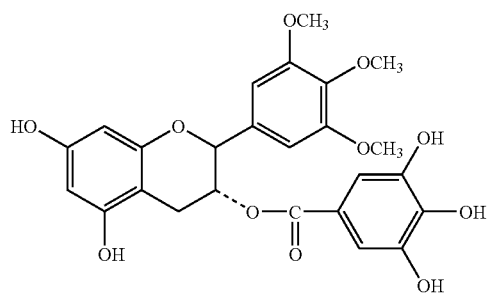

SR 13195:

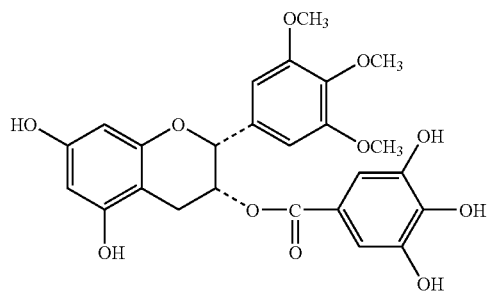

SR 13196:

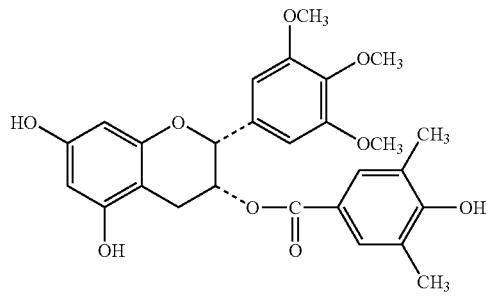

SR 13197:

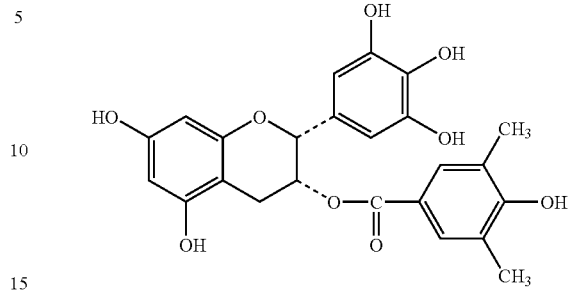

SR 13198:

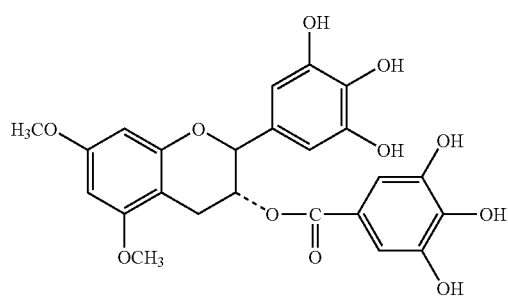

SR 13199:

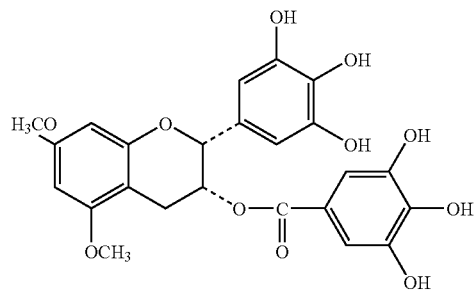

SR 13200:

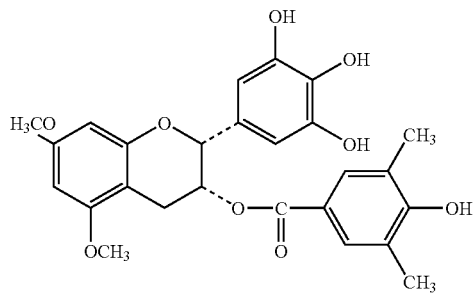

SR 13911:

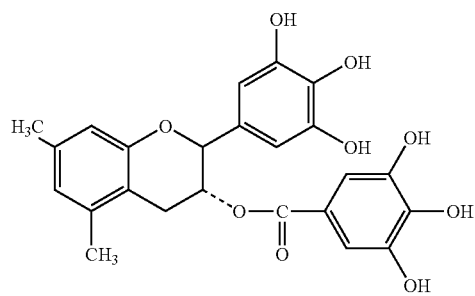

SR 13912:
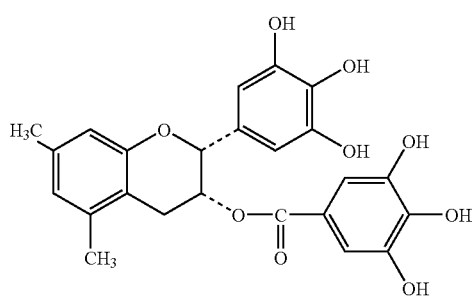
SR 13913:
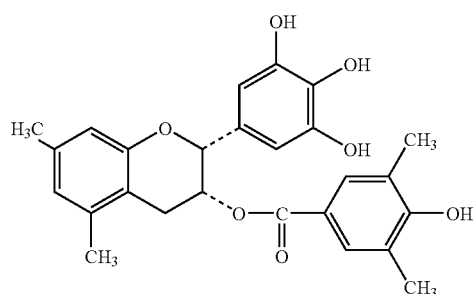
SR 13915:
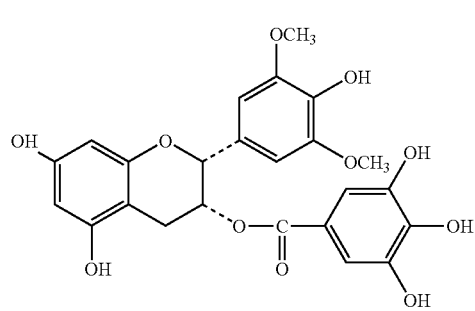
SR 13916:
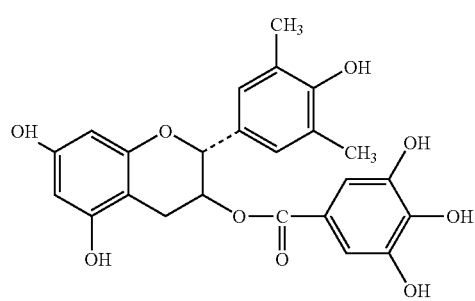
SR 13917:
SR 13918:
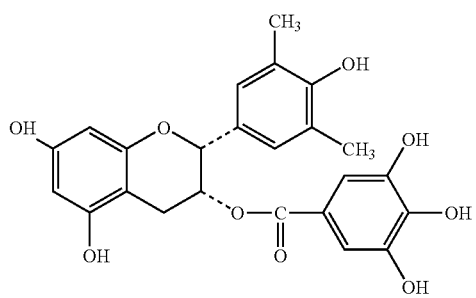
SR 13919:
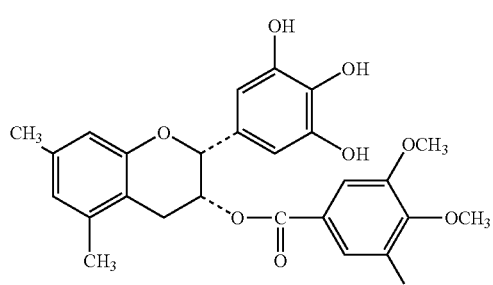
SR 13920:
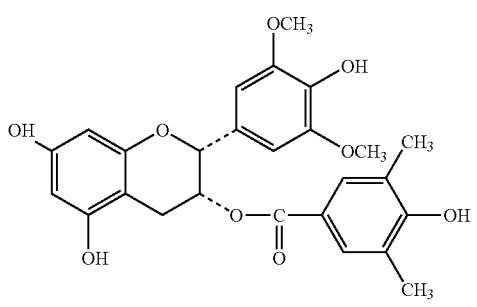
SR 13921:
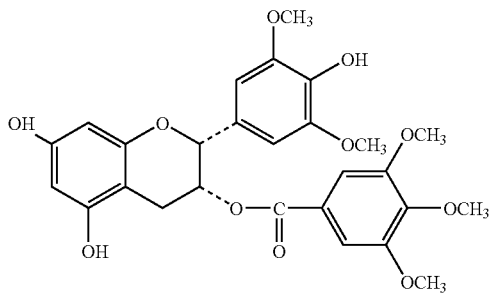

In another embodiment, a compound is provided having the structure of formula (II)

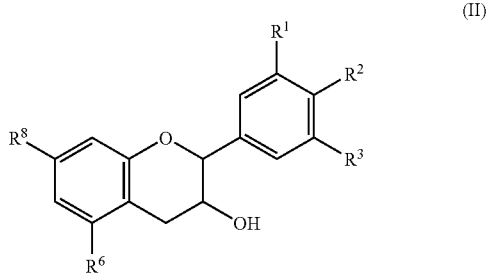

(II)

wherein:

$R^1$, $R^2$, and $R^3$ are selected from the group consisting of hydroxyl; alkyl, preferably $C_1$–$C_6$ alkyl, particularly $C_1$–$C_6$ alkyl, with methyl preferred; halo; sulfhydryl; alkoxy, preferably $C_1$–$C_6$ alkoxy, such as methoxy and ethoxy, with methoxy preferred; and aryloxy, preferably $C_5$–$C_{12}$ aryloxy, with phenoxy preferred. The alkoxy and aryloxy substituents are optionally heteroatom-containing and/or may be substituted with one or more, typically one or two substituents. As noted above, any substituents should not be detrimental to the therapeutic efficacy of the compound, nor should they be reactive with or otherwise interact adversely with other components of the pharmaceutical composition in which the compound is contained. Substituents include functional groups, hydrocarbyl groups, and combinations thereof as described in part (I) of this section.

In addition, either $R^1$ and $R^2$, or $R^2$ and $R^3$, can be linked to form a cyclic structure, which typically, although not necessarily, is selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents such as those enumerated above and zero to 3 heteroatoms. For example, either $R^1$ and $R^2$, or $R^2$ and $R^3$, can be joined to form a lower alkylene linkage, e.g., —(CH$_2$)$_3$— or —(CH$_2$)$_3$—, a lower alkylene linkage substituted with a substituent as described above, a lower heteroalkylene linkage, e.g., —O—CH$_2$—O—, —CH$_2$—O—CH$_2$, or —CH$_2$—NH—CH$_2$, in which case the remaining R group, i.e., $R^1$ or $R^3$, is hydroxyl, $C_1$–$C_6$ alkoxy, or aryloxy.

$R^6$ and $R^8$ are selected from the group consisting of: hydrogen; hydroxyl; alkyl, preferably $C_1$–$C_6$ alkyl, such as methyl and ethyl, with methyl preferred; alkoxy, preferably $C_1$–$C_6$ alkoxy, such as methoxy and ethoxy, with methoxy preferred; and aryloxy, preferably $C_5$–$C_{12}$ aryloxy, with phenoxy preferred.

In a further embodiment, EGCG analogs are provided wherein the analogs contain at least one modification relative to EGCG per se that results in an $IC_{50}$ of less than 60 when using the analogs are evaluated for their ability to inhibit growth in a breast cancer cell line using the 3-(4,5-dimethylthiazol-2-yl)-2,5-diphenyltetrazolium bromide (MTT) assay in a protocol provided by the manufacturer (Promega, Madison, Wis.). Such compounds are useful as precursors for the compounds of formulae (I) and (II), and possibly as therapeutic agents, such as chemotherapeutic and chemopreventive agents.

A compound of the invention may be administered in the form of a salt, ester, amide, prodrug, active metabolite, analog, or the like, provided that the salt, ester, amide, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

For example, acid addition salts may be prepared from a free base (e.g., a compound containing a primary amino group) using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of any acidic moieties that may be present may be carried out in a similar manner using a pharmaceutically acceptable base such as sodium hydroxide, potassium hydroxide, ammonium hydroxide, calcium hydroxide, trimethylamine, or the like. Preparation of esters involves reaction of a hydroxyl group with an esterification reagent such as an acid chloride. Amides may be prepared from esters, using suitable amine reactants, or they may be prepared from an anhydride or an acid chloride by reaction with ammonia or a lower alkyl amine. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

In addition, those novel compounds containing chiral centers can be in the form of a single enantiomer or as a racemic mixture of enantiomers. In some cases, i.e., with regard to certain specific compounds illustrated herein, chirality (i.e., relative stereochemistry) is indicated. In other cases, it is not, and such structures are intended to encompass both the enantiomerically pure form of the compound shown as well as a racemic mixture of enantiomers. Preparation of compounds in enantiomerically form may be carried out using an enantioselective synthesis; alternatively, the enantiomers of a chiral compound obtained in the form of the racemate may be separated post-synthesis, using routine methodology.

Other derivatives and analogs of the active agents may be prepared using standard techniques known to those skilled in the art of synthetic organic chemistry, or may be deduced by reference to the pertinent literature.

The compounds of the invention may be readily synthesized using straightforward techniques. Preferred synthetic methods include the enantioselective synthesis described in Zaveri (2001) *Organic Letters* 3(6):843–846, and the syntheses shown schematically herein in FIGS. 1–4.

III. Pharmaceutical Formulations and Modes of Administration:

The novel compounds may be conveniently formulated into pharmaceutical formulations composed of one or more of the compounds in association with a pharmaceutically acceptable carrier. See *Remington: The Science and Practice* of Pharmacy, 19th Ed. (Easton, Pa.: Mack Publishing Co., 1995), which discloses typical carriers and conventional methods of preparing pharmaceutical formulations.

The compounds of the invention may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the compound administered will, of course, be dependent on the particular active agent, the condition or disorder being treated, the severity of the condition or disorder, the subject's weight, the mode of administration and other pertinent factors known to the prescribing physician. Generally, however, dosage will be in the range of approximately 0.001 mg/kg/day to 100 mg/kg/day, more preferably in the range of about 0.1 mg/kg/day to 10 mg/kg/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, $19^{th}$ Ed. (Easton, Pa.: Mack Publishing Co., 1995).

As the present compounds are orally active, oral dosage forms are generally preferred, and include tablets, capsules, caplets, and nonaqueous solutions, suspensions and or syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, $19^{th}$ Ed. (1995) cited supra, which describes materials and methods for preparing encapsulated pharmaceuticals.

Oral dosage forms, whether tablets, capsules, caplets, or particulates, may, if desired, be formulated to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds of the invention may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compositions will generally be administered orally, parenterally, or transdermally, other modes of administration are suitable as well. For example, administration may be rectal or vaginal, preferably using a suppository thatcontains, in addition to the active agent, excipients such cocoa butter or a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol. Transdermal administration is also a suitable delivery route for compounds of the invention.

IV. Utility:

The compounds of the invention are useful as chemotherapeutic and chemopreventive agents.

The compounds show promise in inhibiting carcinogenesis, and also in inhibiting the growth of tumor cells that have already been transformed. In particular, the compounds of the invention can act as antioxidants and inhibit the production of harmful free radicals that can cause DNA damage. In addition, the compounds can induce apoptosis in tumor cells. Further, the compounds can provide protective effects for normal cells while inhibiting the growth or killing cancerous cells The compounds are useful in the treatment of both primary and metastatic solid tumors and carcinomas of, without limitation, the breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, germ cells, and ovaries; embryo and fetus; male genital tract including prostate, seminal vesicles, testes, and germ cells; endocrine glands including thyroid, adrenal, and pituitary; skin (including hemangiomas, melanomas, sarcomas arising from bone or soft tissues and Kaposi's sarcoma); and the brain, nerves, eyes, and meninges (including astrocytomas, gliomas, glioblastomas, retinoblastomas, neuromas, neuroblastomas, Schwannomas, and meningiomas). The compounds are also useful in treating solid tumors arising from hematopoietic malignancies such as leukemias, including chloromas, plasmacytomas, plaques and tumors of mycosis fungoides, and cutaneous T-cell lymphoma/leukemia; and lymphomas, including both Hodgkin's and non-Hodgkin's lymnphomas. The compounds are of particular use in treating cancers of the breast, ovary, prostate, liver, lung, and pancreas, including drug-resistant forms of these cancers. Efficacy against drug-resistant cancers represents an important advance in the art, as a major problem affecting the efficacy of chemotherapy regimens is the evolution of cancer cells that, upon exposure to a chemotherapeutic drug, become resistant to a multitude of structurally unrelated drugs and therapeutic agents.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

V. Experimental:

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

$^1$H and $^{13}$C NMR spectra were recorded on a Varian Gemini 300 MHz spectrometer (at 300 MHz and 75 MHz, respectively) and are internally referenced to chloroform at δ 7.27 ppm. Data for $^1$H NMR are reported as follows: chemical shift (δ ppm), multiplicity (br=broad, s=singlet, d=doublet, t=triplet, q=quartet, m=multiplet, exch=proton exchanged on addition of $D_2O$), coupling constant (Hz), integration, and assignment. Data for $^{13}$C are reported in terms of chemical shift. IR spectra were recorded on a Perkin-Elmer 1610 spectrometer and are reported in terms of frequency of absorption ($cm^{-1}$). Mass spectra were obtained using a ThermoFinnigan LCQ Duo LC/MS/MS instrument and an electrospray ionization probe. Thin-layer chromoatgraphy was run on Analtech Uniplate silica gel TLC plates. Flash chromatography was carried out using silica gel, Merck grade 9385, 230–400 mesh. Reverse phase chromatography was carried out using C18 reverse phase silica gel, purchased from Baker. Microwave irradiation of reaction mixtures were carried out in capped vials in the Personal Chemistry Microwave Irradiator, Smith Creator.

2',4',6'-trihydroxyacetophenone, 3,4,5-trimethoxybenzaldehyde, 3,5-dimethylphenol and methyl gallate were purchased from Aldrich Chemical Company. 3,5-dimethoxy-2-hydroxyacetophenone and 3,5-dimethyl-4-benzyloxybenzoic acid was purchased from Lancaster. Dess Martin periodinane was purchased from Omega Inc. (Canada). Tetrahydrofuran was distilled from benzophenone ketyl before use.

EXAMPLE 1

SYNTHESIS OF trans-5,7-DIHYDROXY-2-(3,4,5-TRI-METHOXY-PHENYL)-3,4-DIHYDRO-2H-CHROMAN-3-YL, 3,4,5-TRIHYDROXY-BENZOIC ACID ESTER (SR 13194)

SR 13194:

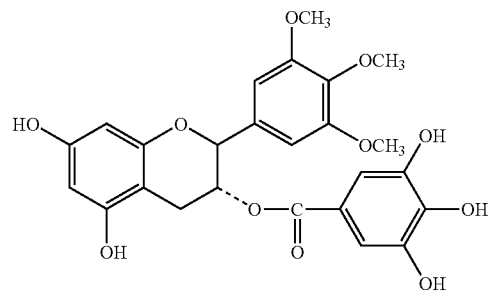

The above compound, a B-ring analog of EGCG, was synthesized according to Scheme 1 (FIG. 1), as follows:

(a) Preparation of 4',6'-bisbenzyloxy-2'-hydroxyacetophenone (2) from 2',4',6'-trihydroxyacetophenone (1): A mixture of 2',4',6'-trihydroxyacetophenone (20 g, 0.12 mol, dried in the oven at 140° C.) and anhydrous potassium carbonate (50 g, 0.36 mol) in hexamethylphosphoramide (160 mL) was treated with benzyl chloride (30 mL, 0.26 mol), and the suspension heated at 90–93° C., under an argon atmosphere, for 1.5 h. The mixture was then cooled and filtered. The filtrate was added to 300 mL ice-cold water and acidified to pH 4 with 6N HCl. The resulting suspension was heated to 70° C. for 1 h, and then cooled at 4° C. for 16 h. The deposited sticky solid was filtered off and washed with water. This solid was air dried, and recrystallized from boiling methanol/acetone (2:1). Cooling the solution afforded the product 8 as off-white crystals (27.55 g, 66.5% yield). $^1$H NMR (300 MHz, CDCl$_3$): δ 2.56 (s, 3H, CH$_3$), 5.06 (s, 4H, CH$_2$), 6.10 and 6.16 (2s, 2H, 3',5'-Ar—H), 7.40 (m, 10H, Ar—H), 14.01 (s, 1H, OH)

(b) Preparation of chalcone 4: A mixture of the acetophenone 2 (2 g, 5.75 mmol) and 3,4,5-trimethoxybenzaldehye (1.69 g, 8.62 mmol) in 10% w/v solution of potassium hydroxide in ethanol was stirred at room temperature for 40 h. The resulting solution deposited a yellow solid, which was collected by filtration and washed with cold ethanol. The solid was dried under high vacuum to afford 2.38 g of product 4 as the first crop. The ethanol filtrate still contained some product and was concentrated down and cooled to afford 0.47 g as a second crop. The combined yield of the two crops was 94%. TLC: hexanes: methylene chloride: ethyl acetate (3:1:1): Rf=0.60; $^1$H NMR (300 MHz, CDCl$_3$): δ 3.67 (s, 6H, OCH$_3$), 3.90 (s, 3H, OCH$_3$), 6.19 (d, J=2.34 Hz, 1H, 8-H), 6.26 (d, J=2.34 Hz, 1H, 6-H), 6.62 (s, 2H, 2', 6'-H), 7.26–7.45 (2m, 10H, Ar—H), 7.71 (d, 1H, CH=CH), 7.82 (d, 1H, CH=CH), 14.23 (s, 1H, OH).

(c) Preparation of the 3-flavene 5: To a solution of the chalcone 4 (2.94 g, 5.59 mmol) in tetrahydrofuran (30 mL) and ethanol (30 mL) was added sodium borohydride (212 mg, 5.59 mmol) at room temperature. The solution was stirred at gentle reflux for 16 hours after which no starting material was observed by TLC. The solution was cooled and evaporated to dryness and the residue was redissolved in methylene chloride. The organic solution was washed with water and brine, dried (MgSO$_4$) and purified by flash chromatography, using stepwise elution with hexanes: ethyl acetate (95:5 to 80:20), to elute the pure product. The fractions containing pure product were pooled, evaporated and dried under vacuum to yield 2.09 g of a colorless thick oil (73% yield). TLC: hexanes:methylene chloride:ethyl acetate (3:1:1): Rf=0.63; $^1$H NMR (300 MHz, CDCl$_3$): δ 3.83 and 3.85 (two s, 9H, OCH$_3$), 4.98 (s, 2H, OCH$_2$Ph), 5.04 (s, 2H, OCH$_2$ Ph), 5.58 (dd, 1H, 3-H), 5.85 (m, 1H, 2-H), 6.15 Ar—H).

(d) Preparation of the 2,3-trans 3-flavanol 6: To a solution of the 3-flavene 5 (2.12 g, 4.17 mmol) in tetrahydrofuran (20 mL) at 0° C. under argon, was added a 1M solution of borane in tetrahydrofuran (33.35 mL, 33.35 mmol) via a dropping funnel. The solution was stirred at room temperature for 4 hours during which time it turned from yellow to colorless. The reaction showed no residual starting material and was cooled down to 0° C. and quenched by dropwise addition of water (2 mL). 3N NaOH (11.8 mL, 35.45 mmol) and 50% H$_2$O$_2$ (2.42 mL, 35.45 mmol) were then added and the solution was warmed to 65° C. for 1 hour and allowed to stir at room temperature for 16 h. The reaction was then diluted with ethyl acetate and washed with water and brine. The organic layer was dried (MgSO$_4$) and evaporated to afford 2.37 g of white solid as crude product. This was purified by flash chromatography, eluting stepwise with hexanes: ethyl acetate (9:1 to 7:3). Fractions containing pure product were pooled and evaporated to afford 0.87 g (40%) of 6 as a translucent white solid. TLC: hexanes: ethyl acetate (6:4): Rf=0.38; $^1$H NMR (300 MHz, CDCl$_3$): δ 2.69 (dd, 1H, 4-H axial), 3.10 (dd, 1H, 4-H equatorial), 3.85 and 3.87 (two s, 9H, OCH$_3$), 4.06 (m, 1H, 3-H), 4.62 (d, 1H, 2-H), 5.00 (s, 2H, CH$_2$OPh), 5.04 (s, 2H, CH$_2$OPh), 6.20 and 6.28 (2d, 2H, 6, 8-Ar—H), 6.67 (s, 2H, 2', 6'-Ar—H), 7.36–7.41 (m, 10H, Ar—H).

(e) Preparation of SR 13194 from 6: 3,4,5-Tribenzyloxybenzoic acid was first converted to its acid chloride by heating a neat solution of the acid (0.375 g, 0.85 mmol) with thionyl chloride (0.99 mL, 13.6 mmol) at 65° C. for 3.5 h. The excess thionyl chloride was evaporated and the residue co-evaporated with hexanes (2×10 mL) and benzene (2×10 mL). The solid acid chloride was dissolved in methylene chloride and added dropwise to a solution of the alcohol 6 (150 mg, 0.28 mmol) and DMAP (51.3 mg, 0.42 mmol) in pyridine (4 mL). The reaction mixture was stirred at room temperature for 16 hours after which it was diluted with methylene chloride and washed with 0.1 N HCl (2×100 mL), water, saturated aqueous NaHCO$_3$ and brine. The organic layer was evaporated to afford 0.497 g of crude ester, which was purified by flash chromatography, eluting the product with hexanes: ethyl acetate (90:10 to 7:3) to afford 0.130 g (48%) of pure ester product as a colorless semisolid. TLC: hexanes: ethyl acetate (6:4): Rf=0.65; $^1$H NMR (300 MHz, CDCl$_3$): δ 2.89 (dd, 1H, 4-H), 3.10 (dd, 1H, 4-H), 3.72 (s, 6H, OCH$_3$), 3.79 (s, 3H, OCH$_3$), 5.04 (m, 11H, OCH$_2$Ph and 3-H), 5.52 (m, 1H, 2-H), 6.31 (d, 2H, 6,8-Ar—H), 6.60 (s, 2H, 2',6'-Ar—H), 7.22–7.37 (m, 25H, Ar—H).

The benzyl protected ester above was dissolved in dioxane (10 mL) and treated with 10% Pd on carbon (70 mg) and hydrogenated at atmospheric pressure using a hydrogen balloon for 5 hours. The mixture was then filtered through an acrodisc filter mounted on a syringe. The filter was washed with methanol and ethyl acetate. The filtrate was evaporated to dryness and the crude product was purified by reverse-phase silica gel chromatography over C18 silica gel, eluting with H$_2$O: methanol (90:10 to 40:60). Fractions containing pure product were concentrated and lyophilized to afford 10 mg of pure SR 13194 as a cream powder. $^1$H NMR (300 MHz, acetone-d$_6$): δ 2.82 (m, 1H, 4-H), 3.10 (m, 1H, 4-H), 3.81 (s, 3H, OCH$_3$), 3.73 and 3.81 (2s, 9H, OCH$_3$), 5.20 (m, 1H, 2-H), 5.45 (m, 1H, 3-H), 6.05 (d, 1H, 8H), 6.15 (d, 1H, 6-H), 6.83 (s, 2H, 2', 6'-Ar—H), 7.10 (s, 2H, 2", 6"-Ar—H), 8.14 (s, OH), 8.22 (m, OH), 8.35 (s, OH). MS (DCI-NH$_3$): 501 (M+H). HRMS: Calcd. 501.4634, Found. 501.1376.

EXAMPLE 2

SYNTHESIS OF cis-5,7-DIHYDROXY-2-(3,4,5-TRIMETHOXY-PHENYL)-3,4-DIHYDRO-2H-CHROMAN-3-YL, 3,4,5-TRIHYDROXY-BENZOIC ACID ESTER (SR 13195)

SR 13195:

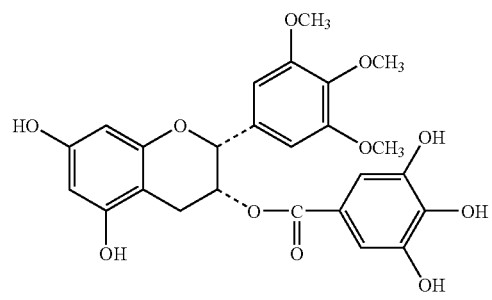

The above compound, also a B-ring analog of EGCG, was synthesized according to Scheme 1 (FIG. 1), as follows:

Preparation of 3-flavanone 7: To a hazy suspension of Dess Martin periodinane (1 g, 2.295 mmol) in dry methylene chloride (10 mL) was added a solution of trans 3-flavanol 6 (0.8 g, 1.53 mmol) in methylene chloride (10 mL) at room temperature. The resulting purple solution was stirred at room temperature for 4 h, after which it was poured into a saturated solution of sodium bicarbonate (60 mL) containing 7 equivalents of sodium thiosulfate (16.06 mmol, 3.98 g) and stirred for 10 minutes. The resulting brown solution was extracted with methylene chloride and the organic layer washed with water and brine, and dried (MgSO$_4$). The filtered solution was then evaporated to afford the crude 3-flavanone 7, which was purified by flash chromatography, using hexanes: ethyl acetate (95:5 to 8:2) to afford 0.432 g (53%) of pure product as a thick, colorless oil. TLC: hexanes: methylene chloride: ethyl acetate (3:1:1): Rf=0.39; $^1$H NMR (300 MHz, CDCl$_3$): δ 3.60 (dd, 2H, 4-Hα and β), 3.79 (s, 6H, OCH$_3$), 3.82 (s, 3H, OCH$_3$), 5.02 (s, 2H, OCH$_2$Ph), 5.04 (s, 2H, OCH$_2$Ph), 5.29 (s, 1H, 2-H), 6.32 and 6.41 (2d, 2H, 6, 8-Ar—H), 6.58 (s, 2H, 2',6'-Ar—H), 7.37–7.40 (m, 10H, Ar—H).

Preparation of the 2,3-cis 3-flavanol 8: To a solution of the 3-flavanone 7 (0.43 g, 0.82 mmol) in dry tetrahydrofuran (10 mL), cooled in a dry ice bath, was added a 1M solution of L-selectride in tetrahydrofuran (7.39 mL, 7.39 mmol) via a syringe under argon. The dry ice bath was then removed and the solution was allowed to stir at room temperature for 8 h. The reaction was again cooled in dry ice, and to this was added 3N NaOH (3.55 mL, 10.66 mmol) and 50% H$_2$O$_2$ (0.72 mL, 10.66 mmol). The solution was stirred for 1 hour at room temperature and then diluted with ethyl acetate. The organic solution was washed with saturated aqueous NaHCO$_3$, water and brine, dried (MgSO$_4$), and evaporated to give the crude alcohol. This was purified by flash chromatography, eluting with hexanes: ethyl acetate (85:15 to 7:3) to afford 0.242 g (52%) of pure product as a greenish yellow foamy solid. TLC: hexanes: ethyl acetate (3:1:1): Rf=0.16 $^1$H NMR (300 MHz, CDCl$_3$): δ 1.75 (d, 1H, OH), 2.95 (dd, 1H, 4-H), 3.05 (dd, 1H, 4-H), 3.86 (s, 3H, OCH$_3$), 3.89 (s, 6H, OCH$_3$), 4.30 (m, 1H, 3-H), 4.95 (broad s, 1H, 2-H), 5.02 (s, 2H, CH$_2$OPh), 5.04 (s, 2H, CH$_2$OPh), 6.28 and 6.31 (two d, 2H, 6,8-Ar—H), 6.75 (s, 2H, 2', 6'-Ar—H), 7.36–7.41 (m, 10H, Ar—H).

Preparation of SR 13195 from the 2,3-cis-3-flavanol 8: The esterification of the 3-flavanol 8 to SR 13195 was carried out as described in Example 1, part (e), with respect to the synthesis of SR 13194, using 0.25 g (0.57 mmol) of 3,4,5-tribenzyloxybenzoic acid and 100 mg (0.19 mmol) of the cis 3-flavanol 8 to afford 79 mg (44%) yield of the benzyl protected ester after flash chromatography. TLC: hexanes: ethyl acetate (6:4): Rf=0.51; $^1$H NMR (300 MHz, CDCl$_3$): δ 3.10 (m, 2H, 4-H), 3.53 (s, 6H, OCH$_3$), 3.80 (m, 3H, OCH$_3$), 5.04 (m, 11H, OCH$_2$Ph and 3-H), 5.69 (m, 1H, 2-H), 6.35 (d, 1H, 8-Ar—H), 6.41 (d, 1H, 6-Ar—H), 6.60 (s, 2H, 2',6'-Ar—H), 7.25–7.38 (m, 25H, Ar—H). The ester was deprotected by catalytic hydrogenation as described in Example 1, part (e), using 172 mg of the ester and 100 mg of 10% Pd on carbon in dioxane (10 mL). The crude product was purified by reverse phase chromatography to afford 24 mg of pure SR 13195 as a fluffy cream powder. MS (DCI-NH$_3$): 501 (M+H).

EXAMPLE 3

SYNTHESIS OF cis-5,7-DIHYDROXY-2-(3,4,5-TRIMETHOXY-PHENYL)-3,4-DIHYDRO-2H-CHROMAN-3-YL, 4-HYDROXY-3,5-DIMETHYL-BENZOIC ACID ESTER (SR 13196)

SR 13196:

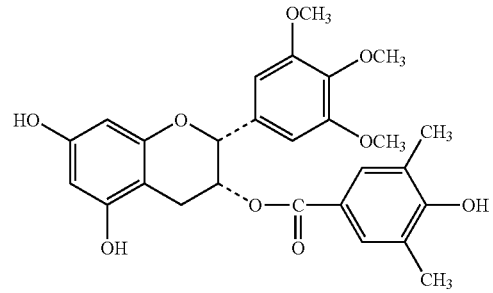

The above compound, a B- and D-ring analog of EGCG, was synthesized according to Scheme 1 (FIG. 1), as follows:

The esterification of the 3-flavanol 8 to SR 13196 was also carried out as described in Example 1, part (e). The acid chloride of 3,5-dibenzyloxy-4-methylbenzoic acid (0.276 g, 1.08 mmol) was prepared as described for SR 13194 and added to a solution of 8 (142 mg, 0.27 mmol) and dimethylamino pyridine (DMAP; 49.5 mg, 0.405 mmol) in dry pyridine. The mixture was stirred for 16 hours and recharged with acid chloride (1.08 mmol) and stirred for an additional 18 h, after which all of 8 was consumed. The reaction was poured into 1N HCl (25 mL) and extracted with methylene chloride. The organic layer was washed with water, saturated NaHCO$_3$, and brine. The organic layer was dried (MgSO$_4$) and evaporated to yield a crude product, which was purified by flash chromatography, eluting the pure ester with methylene chloride: ethyl acetate (99:1) to afford 110 mg (53%) of the benzyl protected ester after flash chromatography. TLC: hexanes: ethyl acetate (6:4): Rf=0.53; $^1$H NMR (300 MHz, CDCl$_3$): δ 2.26 (s, 6H, CH3), 3.11 (m, 2H, 4-H), 3.74 (s, 6H, OCH3), 3.80 (m, 4H, OCH3 and 3-H), 4.80 (s, 2H, 2", 6"-H), 5.05 (m, 6H, CH2OPh), 5.65 (m, 1H, 2-H), 6.32 (two d, 2H, 6,8-H), 6.71 (s, 2H, 2', 6'-H), 7.35–7.42 (m, 15H, Ar—H).

The ester was deprotected by catalytic hydrogenation as described in Example 1, part (e), using 110 mg of the ester and 50 mg of 10% Pd black in dioxane (10 mL). The crude product was purified by normal phase flash chromatography, eluting the product with methylene chloride: ethyl acetate (9:1 to 8:2). Fractions containing pure product were evaporated and dried to afford 53 mg of pure SR 13196 as a flaky crystalline white solid. TLC: methylene chloride: ethyl acetate (7:3): Rf=0.33; $^1$H NMR (300 MHz, CDCl$_3$): δ 2.20 (s, 6H, CH$_3$), 3.02 (m, 2H, 4-H), 3.65 (s, 3H, OCH$_3$), 2.79 (s, 6H, OCH$_3$), 5.21 (s, 1H, 3-H), 5.60 (broad s, 1H, 2-H), 6.05 (m, 2H, 6,8-Ar—H), 6.90 (s, 2H,2', 6'-Ar—H), 7.57 (s, 2H,2", 6"-Ar—H), 7.98 (s, 1 H, OH), 8.03 (s, 1H, OH), 8.25 (s, 1H, OH). MS (ESI): 495 (M−H); HRMS (M+H): Calcd. 497.5188, Found. 497.1826.

EXAMPLE 4

SYNTHESIS OF cis-5,7-DIHYDROXY-2-(3,4,5-TRIMETHOXYPHENYL)-3,4-DIHYDRO-2H-chroman-3-yl, 4-Methoxy-3,5-dimethyl-benzoic acid ester (SR 13197)

SR 13197:

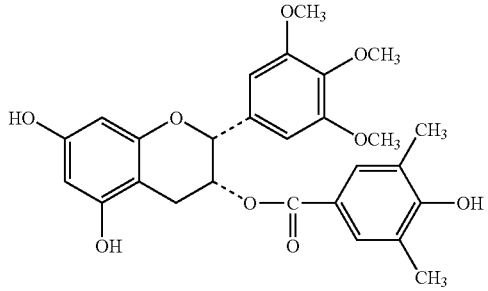

The above compound, a D-ring analog of EGCG, was synthesized according to Scheme 2 (FIG. 2), as follows:

(a) Preparation of 3,4,5-tribenzyloxybenzaldehyde 12 from methyl gallate 9: A mixture of methyl gallate 9 (10 g, 53 mmol) and potassium carbonate (45 g, 320 mmol) in DMF (120 mL) was treated with benzyl bromide (210 mmol, 25.7 mL) and stirred at 40° C. under an argon atmosphere for 24 h. The reaction mixture was filtered and the filtrate evaporated to dryness. The residue was dissolved in minimum amount of methylene chloride and diluted with an equal volume of hexanes and loaded onto a short silica gel pad in a sintered glass funnel. The silica was eluted with hexanes (300 mL) to remove excess benzyl bromide and the eluant discarded. The product was then eluted with methylene chloride: hexanes (1:1,300 mL) followed by methylene chloride (500 mL) and the eluants combined and evaporated to afford pure benzyl product 10 as an off-white solid (100% yield). $^1$H NMR (300 MHz, CDCl$_3$): δ 3.88 (s, 3H, CH$_3$), 5.11 and 5.13 (2s, 6H, OCH$_2$), 7.35–7.41 (m, 17H, Ar—H).

To a solution of 3,4,5-tribenzyl-methyl gallate 10 (10 g, 22 mmol) in dry tetrahydrofuran (75 mL) was added solid lithium aluminum hydride (1.25 g, 33 mmol) in small portions. The suspension was heated to reflux under argon for 2h. The reaction was cooled to 0° C. and carefully quenched with the dropwise addition of water. The slurry was then extracted with ethylacetate/hexanes. The organic solution was dried with saturated brine, followed by anhydrous magnesium sulfate, filtered and evaporated to afford the pure. alcohol 11 as a white solid (8.9 g, 95% yield). $^1$H NMR (300 MHz, CDCl$_3$): δ 4.6 (d, 2H, CH$_2$), 5.04 and 5.11 (2s, 6H, OCH$_2$), 6.67 (s, 2H, 2,6-Ar—H), 7.25–7.43 (m, 15H, Ar—H).

To a solution of 3,4,5-tribenzyloxy-benzyl alcohol 11 (8.9 g, 21 mmol) in methylene chloride (200 mL) at 0° C. was added pyridinium chlorochromate (5.43 g, 25 mmol) in small portions with vigorous stirring. The cooling was discontinued and reaction stirred at room temperature for 4 h. The dark brown suspension was filtered over a long pad of silica gel in a sintered glass funnel, and eluted with methylene chloride, until all the pure product eluted out. The organic filtrate was evaporated down to give the pure product 12 as a soft white solid (8.1 g, 91.5% yield). $^1$H NMR (300 MHz, CDCl$_3$): δ 5.16 (s, 6H, OCH$_2$), 7.18 (s, 2H, 2,6-Ar—H), 7.26–7.41 (m, 15H, Ar—H), 9.80 (s, 1H, CHO).

(b) Preparation of chalcone 13: A mixture of 4,6-dibenzyloxy-2-hydroxy-acetophenone 2 (15 g, 0.043 mol) and 3,4,5-tribenzyloxybenzaldehyde 12 (20.1 g, 0.047 mol) in ethanol (400 mL) was placed in a three-necked flask fitted with an overhead stirrer and condenser. Piperidine (80 mL) was then added and the mixture was heated to reflux for 24 h. A yellow solid precipitated out. The reaction mixture was cooled and filtered to afford a yellow solid, which was washed with cold ethanol and dried to afford the chalcone 13 as a yellow solid (60% yield). TLC: methylene chloride: Rf=0.51; $^1$H NMR (300 MHz, CDCl$_3$): δ 4.87 (s, 4H, CH$_2$OPh), 5.12 (m, 6H, CH$_2$OPh), 6.18 (d, 1H, 3'-Ar—H), 6.25 (d, 1H, 5'-Ar—H), 6.70 (s, 2H, 2, 6-Ar—H), 7.19–7.45 (m, 25H, OBn-Ar—H), 7.66 (d, 1H, C(O)—CH=CH—), 7.78 (d, 1H, C(O)—CH=CH—), 14.21 (s, 1H, OH). $^{13}$C NMR (75 MHz, CDCl$_3$): δ 70.39, 71.20, 75,26, 93.07, 95.22, 108.44, 127.10–128.83, 130.84, 135.80, 135.94, 136.89, 142.46, 152.92, 161.55, 165.24, 168.17, 192.63. Anal. Calcd. for C$_{50}$H$_{42}$O$_7$ (754.88): C, 79.56; H, 5.61. Found: C, 79.47; H, 5.64.

(c) Preparation of 3-flavene 14: The 3-flavene 14 was synthesized by the same procedure as for the synthesis of 3-flavene 5, (Scheme 1), using NaBH$_4$/THF/EtOH. The 3-flavene was typically isolated in 50–60% yield as a colorless thick liquid. TLC: methylene chloride: hexanes (8:2): Rf=0.53; $^1$H NMR (300 MHz, CDCl$_3$): δ 4.99, 5.03, 5.05, 5.09 (4s, 10 H, CH$_2$OPh), 5.53 (dd, J=9.95 and 3.29 Hz, 1H, 3-H), 5.72 (dd, J=3.24 and 1.95 Hz, 1H, 2-H), 6.13 and 6.20 (2d, J=2.17, 2H, 6, 8-Ar—H), 6.78 (s, 2H, 2', 6'-Ar—H), 6.86 (dd, J=9.86 and 1.57 Hz, 1H, 4-H), 7.25–7.41 (m, 25H, Ar—H).

(d) Preparation of 2,3-trans 3-flavanol 15: The trans 3-flavanol 14 was synthesized by the same procedure as for the synthesis of flavanol 6 (Scheme 1), using BH$_3$/THF. The trans 3-flavanol was typically isolated in 70% yield as a white solid. TLC: methylene chloride: hexanes (8:2): Rf=0.13; $^1$H NMR (300 MHz, CDCl$_3$): δ 2.64 (dd, J=16.45 and 8.88 Hz, 1H, 4Haxial), 3.10 (dd, J=16.42 and 5.68 Hz, 1H, 4-Hequatorial), 3.96 (m, 1H, 3-H), 4.61 (d, J=8.12 Hz, 1H, 2-H), 5.05 (m, 10H, CH$_2$OPh), 6.20 and 6.28 (2s, 2H, 6,8-Ar—H), 6.73 (s, 2H, 2', 6'-Ar—H), 7.25–7.41 (m, 25H, Ar—H). MS (DCI-NH$_3$): 757 (M+H), 774 (M+NH$_4$).

(e) Preparation of 3-flavanone 16: The 3-flavanone 16 was synthesized by Dess Martin oxidation of the 3-flavanol 15 in an identical manner as for the synthesis of 3-flavanone 7 (Scheme 1), in 50–60% yields. TLC: methylene chloride: Rf=0.37; $^1$H NMR (300 MHz, CDCl$_3$): δ 3.41 (d, J=21.3 Hz, 1H, 4-H), 3.39 (d, J=21.3 Hz, 1H, 4-H), 5.03 (m, 10H, CH$_2$OPh), 5.24 (s, 1H, 2-H), 6.35 and 6.37 (2s, 2H, 6,8-Ar—H), 6.67 (s, 2H, 2', 6'-Ar—H), 7.25–7.41 (m, 25H, Ar—H).

(f) Preparation of the 2,3-cis 3-flavanol 17: The cis 3-flavanol 17 was prepared by the L-selectride reduction of the 3-flavanone 16 in the same manner as for the synthesis of flavanol 8 (Scheme 1) in 60–70% yields. TLC: hexanes: ethyl acetate (8:2): Rf=0.27; $^1$H NMR (300 MHz, CDCl$_3$): δ 1.61 (broad s, 1H, OH), 2.92 (dd, J=17.13 and 4.40 Hz, 1H, 4-H), 3.02 (dd, J=17.64 and 2.27 Hz, 1H, 4-H), 4.21 (m, 1H, 3-H), 4.90 (broad s, 1H, 2-H), 5.03 (s, 4H, CH$_2$OPh), 5.06 (s, 2H, CH$_2$OPh), 5.14 (s, 4H, CH$_2$OPh), 6.28 (s, 2H, 6,8-Ar—H), 6.81 (s, 2H, 2', 6'-Ar—H), 7.25–7.41 (m, 25H, Ar—H). MS (DCI-NH$_3$): 757 (M+H), 774 (M+NH$_4$).

(g) Preparation of SR 13197 from cis 3-flavanol 17: To a solution of 4-benzyloxy-3,5-dimethylbenzoic acid (0.138 g, 0.53 mmol), EDC (305 mg, 1.59 mmol), HOBt (143.23 mg, 1.06 mmol), DMAP (129.50 mg, 1.06 mmol) and triethylamine (0.185 mL, 1.325 mmol) in methylene chloride (7 mL) was added a solution of 17 (200 mg, 0.265 mmol) in methylene chloride (3 mL). The solution was stirred at room temperature for 60 h, after which no starting flavanol was seen by TLC. The reaction was diluted with methylene chloride (100 mL) and washed with 0.1 N HCl, saturated NaHCO$_3$, water and brine. The organic layer was dried (MgSO$_4$) and evaporated to give 0.36 g of crude product which was purified by flash chromatography, eluting the product as a pure fraction, with methylene chloride: hexanes (7:3). Fractions containing pure product were pooled and evaporated to afford 0.166 g (63%) yield of the protected ester intermediate. TLC: hexanes: ethyl acetate (6:4): Rf=0.72; $^1$H NMR (300 MHz, CDCl$_3$): δ 2.23 (s, 6H, CH$_3$), 3.11 (m, 2H, 4-H), 4.59 (d, J=2.4 Hz, 3-H), 4.99 (m 12H, CH$_2$OPh,), 5.62 (s, 1H, 2-H), 6.31 (d, J=2.4 Hz, 8-H), 6.35 (d, J=2.4 Hz, 6-H), 6.82 (s, 2H, 2',6'-H), 7.34 (m, 30H, Ar—H), 7.68 (s, 2H, 2",6"-H); MS (ESI) 1017 (M+Na).

SR 13197 was then prepared from the protected ester above by catalytic hydrogenation with Pd black using the same procedure as for the synthesis of SR 13196 (Scheme 1). $^1$H NMR (300 MHz, acetone-d$_6$): δ 2.21 (s, 3H, CH$_3$), 2.26 (s, 3H, CH$_3$), 2.98–3.01 (m 2H, 4-H), 5.09 (s, 1H, 3-H), 5.46–5.49 (m, 1H, 2-H), 6.02 (d, J=2.4 Hz, 1H, 8-H), 6.04 (d, J=2.4 Hz, 1H, 6-H), 6.63 (s, 2H, 2",6"-H), 7.52 (s, 2H, 2',6'-H), 7.65 (s, 2H, OH).

EXAMPLE 5

SYNTHESIS OF trans-5,7-DIMETHOXY-2-(3,4,5-TRIHYDROXY-PHENYL)-3,4-DIHYDRO-2H-CHROMAN-3-YL, 3,4,5-TRIHYDROXY-BENZOIC ACID ESTER (SR 13198)

SR 13198:

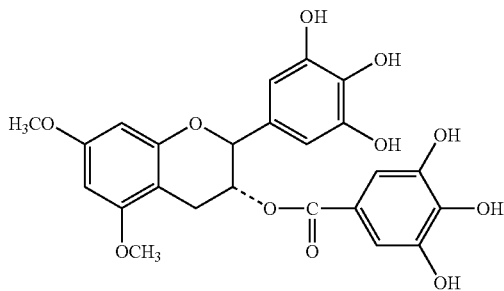

The above compound, an A-ring analog of EGCG, was synthesized according to Scheme 3 (FIG. 3), as follows:

(a) Preparation of (2E)-1-(2-hydroxy-4,6-dimethoxyphenyl)-3-(3,4,5-tribenzyloxyphenyl)prop-2-en-1-one (19): To a suspension of NaH (1.63 g, 40.78 mmol, 60% in mineral oil w/w) in 50 mL of freshly distilled DMF, was portion wise added 4,6-dimethyoxy-2-hydroxyacetophenone 18 (5 g, 25.50 mmol) at room temperature. The mixture was left to stir for 1 hour until all H2 evolution was ceased. Tribenzyloxybenzaldehyde 12 (13 g, 30.60 mmol) was then added all at once and the mixture continued to stir for an additional 30 minutes, after which the solution gradually became dark red. The mixture was diluted with water and a yellow solid precipitated from solution. The solid thus obtained was filtered off and washed several times with cold methanol, and dried under reduced pressure (15 mmHg at room temperature) overnight to provide 14.12 g (92% yield) of pure chalcone 19. $^1$H NMR (300 MHz, CDCl$_3$): δ 3.81 (s, 3H, OCH$_3$), 3.84 (s, 3H, OCH$_3$), 5.12 (s, 2H, OCH$_2$Ph), 5.16 (s, 4H, OCH$_2$Ph), 5.94 (d, J=2.7 Hz, 1H, CH=CH), 6.10 (d, J=2.7 Hz, 1H, CH=CH), 6.88 (s, 2H, 2',6'-Ar—H), 7.26–7.44 (m, 17H, Ar—H, 6,8-H), 14.25 (s, 1H, OH). $^{13}$C NMR (CDCl$_3$): 55.59, 55.80, 71.34, 75.31, 91.29, 93.83, 106.34, 108.32, 126.87, 127.31, 127.46, 127.94, 127.98, 128.20, 128.58, 131.13, 136.86, 137.55, 140.90, 142.30, 153.02, 162.41, 166.19, 168.34, 192.37.

(b) Preparation of 5,7-dimethoxy-2-(3,4,5-tribenzyloxyphenyl)-2H-chromene (20)

The 3-flavene 20 was synthesized by the same procedure as for the synthesis of 3-flavene 5, (Scheme 1), using NaBH$_4$/THF/EtOH. 20 was isolated in 52% yield as a white solid after flash chromatography using methylene chloride. $^1$H NMR (300 MHz, CDCl$_3$): δ 3.75 (s, 3H, OCH$_3$), 3.78 (s, 3H, OCH$_3$), 5.02 (s, 2H, OCH$_2$Ph, 5.09 (s, 4H, OCH$_2$Ph), 5.52 (dd, J=3.6, 9.6 Hz, 1H, 4-H), 5.69–5.72 (m, 1H, 3-H), 6.05 (s, 2H, 2',6'-Ar—H), 6.76 (s, 2H, 6,8-Ar—H), 6.78 (dd, J=1.8, 9.6 Hz, 1H, 2-H), 7.24–7.43 (m, 15H, Ar—H). $^{13}$C NMR (CDCl$_3$): 55.61, 55.86, 71.46, 75.43, 77.52, 92.15, 94.01, 104.59, 107.21, 119.20, 119.85, 127.78, 127.97, 128.06, 128.36, 128.66, 128.74, 136.69, 137.29, 138.14, 138.79, 153.15, 155.06, 156.52, 161.53.

(c) Preparation of (2,3-trans)-5,7-dimethoxy-2-(3,4,5-tribenzyloxyphenyl)chroman-3-ol (21): The flavanol 21 was synthesized by the same hydroboration/oxidation sequence from 20, as used for 6, yielding exclusively the 2,3-trans alcohol 21 as a white solid in 83% yield after silica gel chromatography, eluting 30% ethyl acetate in hexanes. $^1$H NMR (300 MHz, CDCl3): δ 1.63 (d, J=3.6 Hz, 1H, OH), 2.55 (dd, J=8.7, 16.5 Hz, 1H, 4-H), 2.98 (dd, J=5.7, 16.5 Hz, 1H, 4-H), 3.74 (s, 3H, OCH$_3$), 3.78 (s, 3H, OCH$_3$), 3.90–4.00 (m, 1H, 3-H), 4.59 (d, J=7.8 Hz, 2-H), 5.05 (s, 2H, OCH$_2$Ph), 5.08 (s, 2H, OCH$_2$Ph), 5.09 (s, 2H, OCH$_2$Ph), 6.10 (d, J=2.4 Hz, 1H, 8-H), 6.12 (d, J=2.4 Hz, 1H, 6-H), 6.73 (s, 2H, 2',6'-H), 7.22–7.43 (m, 15H, Ar—H). $^{13}$C NMR (CDCl3) 27.57, 55.61, 55.74, 68.50, 71.49, 75.42, 77.43, 82.04, 92.23, 93.24, 101.78, 107.05, 127.78, 128.05, 128.16, 128.39, 128.71, 128.76, 133.57, 137.09, 138.01, 153.28, 155.30, 159.00, 160.00.

(d) Preparation of SR 13198: The hexabenzyloxy-protected precursor of SR 13198 was prepared from 21 as follows. A mixture of 21 (400 mg, 0.66 mmol), 3,4,5-tribenzyloxy-benzoic acid (585 mg, 1.32 nmmol), EDC (761 mg, 3.97 mmol), 1-hydroxybenzotriazole HOBt (358 mg, 2.65 mmol), DMAP (323 mg, 2.65 mmol), triethylamine (461 μL, 3.31 mmol) and methylene chloride (15 mL) was stirred at room temperature under argon for 18–24 hours after which all starting alcohol was consumed as confirmed by TLC. The mixture was then poured into 20 mL of 2N HCl solution, extracted with ethyl acetate, dried over magnesium sulfate and evaporated to dryness. The crude thus obtained was purified by flash chromatography on silica gel using 20% of ethyl acetate in hexanes to afford a white solid (650 mg, 96% yield). $^1$H NMR (300 MHz, CDCl3): 2.74 (dd, J=6.6, 17.1 Hz, 1H, 4-H), 2.95 (dd, J=5.7, 17.1 Hz, 1H, 4-H), 3.79 (s, 3H, OCH$_3$), 3.81 (s, 3H, OCH$_3$), 4.98–5.22 (m, 13H, OCH$_2$Ph, 3-H), 5.38–5.44 (m, 1H, 2-H), 6.15 (d, J=1.5 Hz, 8-H), 6.21 (d, J=1.5 Hz, 6-H), 6.71 (s, 2H, 2',6'-H), 7.20–7.45 (m, 32H, Ar—H 2", 6"-H).

The hydrogenolysis of this hexabenzyloxy ester as described above for the syntheses of Examples 1–4 gave the desired polyphenol SR 13198 in 86% yield as a yellowish solid after reverse phase chromatography using a gradient of methanol in water (from 7/3 then 1/1 then 3/7 respectively). $^1$H NMR (300 MHz, acetone-d6): 2.75–2.79 (m, 2H, 4-H), 3.77 (s, 3H, OCH₃), 3.78 (s, 3H, OCH₃), 5.16 (d, J=4.8 Hz, 1H), 5.40 (q, J=4.8 Hz, 1H), 6.13 (d, J=2.4 Hz, 1H, 8-H), 6.15 (d, J=2.4 Hz, 1H, 6-H), 6.46 (s, 2H, 2',6'-H), 7.03 (s, 2H, 2", 6"-H), 7.25 (s, 1H, OH), 7.84 (s, 2H, OH), 7.99 (s, 1H, OH), 8.16 (s, 2H, OH). MS (ESI, negative ion mode) 485 (M-1), 971 (2M-1).

EXAMPLE 6

SYNTHESIS OF cis-5,7-DIMETHOXY-2-(3,4,5-TRIHYDROXY-PHENYL)-3,4-DIHYDRO-2H-CHROMAN-3-YL, 3,4,5-TRIHYDROXY-BENZOIC ACID ESTER (SR 13199)

SR 13199:

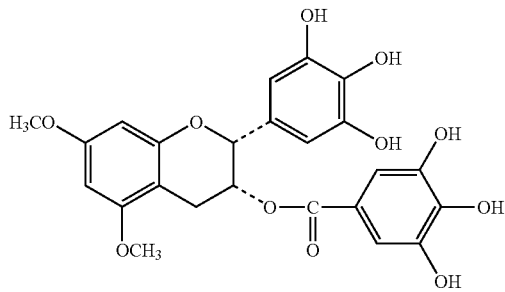

The above compound, also an A-ring analog of EGCG, was synthesized according to Scheme 3 (FIG. 3), as follows:

(a) Preparation of 5,7-dimethoxy-2-(3,4,5-tribenzyloxyphenyl)-2H-chromen-3(4H)-one (22): 3-Flavanone 22 was prepared by the Dess-Martin periodinane oxidation of 21 using the same procedure used for the synthesis of 7. The white crystalline 3-flavanone 22 was obtained in 80% yield after flash chromatography on silica gel using 20% of ethyl acetate in hexanes. ¹H NMR (300 MHz, CDCl₃): δ 3.43 (d, J=21.4 Hz, 1H, 4-H), 3.53 (dd, J=0.9, 21.4 Hz, 1H, 4H), 3.79 (s, 3H, OCH₃), 3.80 (s, 3H, OCH₃), 5.01 (s, 2H, OCH₂Ph), 5.04 (s, 2H, OCH₂Ph), 5.05 (s, 2H, OCH₂Ph), 5.24 (s, 1H, 2-H), 6.18 (d, J=2.4 Hz, 1H, 8-H), 6.28 (d, J=2.4 Hz, 1H, 6H), 6.67 (s, 1H, 2'-H), 6.68 (s, 1H, 6'-H ), 7.24–7.39 (m, 15H, Ar—H).

(b) Preparation of (2,3-cis)-5,7-dimethoxy-2-(3,4,5-tribenzyloxyphenyl) chroman-3-ol (23): A solution of 3-flavanone 22 (1.87 g, 3.10 mmol) in 30 mL of tetrahydrofuran was added dropwise to a cooled (−78° C.) solution of dried (200° C. at 0.2 mmHg for 18 h) lithium bromide (1.6 g, 18.4 mmol) and L-selectride® (25 mL, 25 mmol, 1M solution in tetrahydrofuran). After complete addition of 22, the dry ice bath was removed and the mixture allowed to warm up to room temperature. The mixture was stirred at room temperature for an additional 15 hours after which most of starting material was reduced as shown by TLC. The reaction mixture was cooled in an ice bath and subjected to an oxidative work up by adding carefully, a solution of H₂O₂ (50 % in water, 15–20 mL) and 20 mL of ethanol. The mixture was diluted with ethyl acetate and water and worked up as usual. The crude material was purified by flash chromatography on silica gel using 30% of ethyl acetate in hexane to give 740 mg of colorless oil (40% yield), which crystallized upon standing. ¹H NMR (300 MHz, CDCl₃): δ 1.77 (d, J=2.8 Hz, 1H, OH), 2.78–2.90 (m, 2H, 4-H), 3.78 (s, 3H, OCH₃), 3.79 (s, 3H, OCH₃), 4.20–4.22 (m, 1H, 3-H), 4.88 (s, 1H, 2-H), 5.03–5.14 (m, 6H, OCH₂Ph), 6.12 (d, J=2.4 Hz, 1H, 8-H), 6.19 (d, J=2.4 Hz, 1H, 6-H), 6.82 (s, 2H, 2',6'-H), 7.24–7.44 (m, 15H, Ar—H). ¹³C NMR (CDCl₃) 27.94, 55.41, 55.49, 66.42, 71.39, 75.24, 77.22, 78.52, 92.26, 93.36, 100.29, 106.20, 127.58, 127.82, 127.92, 128.17, 128.17, 128.58, 133.81, 137.02, 137.85, 138.40, 153.06, 155.05, 159.26, 159.73.

(c) Preparation of (2,3-Cis)-5,7-dimethoxy-2-(3,4,5-trihydroxyphenyl)-3,4-dihydro-2H-chromen-3-yl (3,4,5-dihydroxybenzoate) SR 13199: A 5 mL thick wall microwave vial was charged with 23 (400 mg, 0.66 mmol), 3,4,5-tribenzyloxybenzoic acid (594 mg, 1.35 mmol), BOP reagent (1.19 g, 2.7 mmol), DMAP (330 mg, 2.7 mmol), diisopropylethylamine (575 μL, 3.3 mmol) and 1 mL of freshly distilled DMF. The vial was sealed and heated in a single mode (MW) Smith Creator™ chamber for 5 minutes at 170° C., after which all starting material was consumed, as shown by TLC. The mixture was diluted with ethyl acetate and 1M solution of HCl. After work up, the crude material was purified by flash chromatography on silica gel with 20% of ethyl acetate in hexane to yield 600 mg of hexabenzyloxy-protected SR 13199 as a colorless oil (89% yield). ¹H NMR (300 MHz, CDCl₃): δ 3.01–3.16 (m, 2H, 4-H), 3.79 (s, 3H, OCH₃), 3.781 (s, 3H, OCH₃), 4.69 (d, J=11.4 Hz, 2H, ), 4.81 (d, J=11.4 Hz, 2H,), 4.81 (d, J=11.4 Hz, 2H), 4.90 (s, 2H), 4.96 (s, 1H), 4.97 (s, 1H), 5.01 (s, 4H), 5.04 (s, 1H), 5.62–5.64 (m, 1H), 6.16 (d, J=2.4 Hz, 1H, 8-H ), 6.29 (d, J=2.4 Hz, 1H, 6-H), 6.74 (s, 2H, 2',6'-H), 7.19–7.35 (m, 32H, Ar—H, 2", 6"-H). Hydrogenolysis of the above intermediate gave SR 13199.

EXAMPLE 7

SYNTHESIS OF cis-5,7-DIMETHOXY-2-(3,4,5-TRIHYDROXY-PHENYL)-3,4-DIHYDRO-2H-CHROMAN-3-YL, 4-METHOXY-3,5-DIMETHYL-BENZOIC ACID ESTER (SR 13200)

SR 13200:

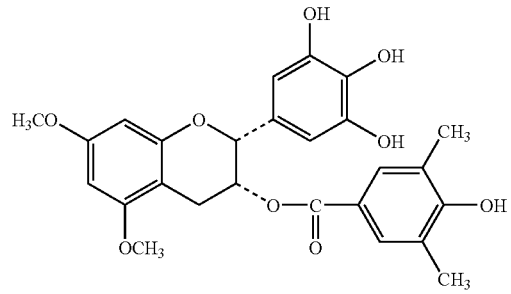

The above compound, an A- and D-ring analog of EGCG, was synthesized according to Scheme 3 (FIG. 3), as follows:

(a) SR 13200 was synthesized by esterification of 23 with 4-benzyloxy-3,5-dimethylbenzoic acid using the same procedure as for the synthesis of SR 13199. The tetrabenzyloxy-protected ester was obtained in 95% yield as colorless viscous oil after flash chromatography using 20% ethyl acetate in hexanes. ¹H NMR (300 MHz, CDCl₃): δ 2.23 (s, 6H, CH₃), 3.01–3.09 (m, 2H, 4-H), 3.79 (s, 3H, OCH₃), 3.782 (s, 3H, OCH₃), 4.59 (s, 1H), 4.60 (s, 1H), 4.82 (d, J=11.4 Hz, 2H), 4.97 (s, 2H), 4.99 (d, J=11.4 Hz, 2H), 5.04 (s, 1H), 5.61–5.69 (m, 1H), 6.13 (d, J=2.4 Hz, 1H), 6.25 (d, J=2.4 Hz, 1H), 6.82 (s, 2H), 7.18–7.38 (m, 22H, Ar—H).

Hydrogenolysis of the above intermediate gave SR 13200 in 16% yield of a pinkish white solid. MS (ESI, positive ion)

505 (M+Na), 986(2M+Na), 1469(3M+Na). MS (ESI, negative ion) 481(M-1), 963(2M-1), 1445(3M-1).

EXAMPLE 8

SYNTHESIS OF trans-5,7-DIMETHYL-2-(3,4,5-TRIHYDROXY-PHENYL)-3,4-DIHYDRO-2H-CHROMAN-3-YL, 3,4,5-TRIHYDROXY-BENZOIC ACID ESTER (SR 13911)

SR 13911:

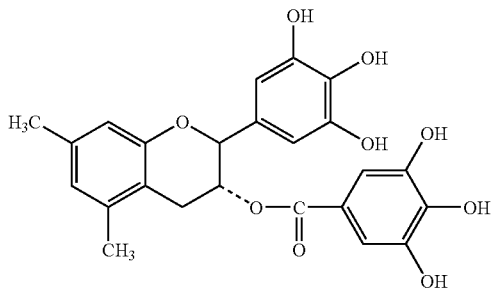

The above compound, an A-ring analog of EGCG, was synthesized according to Scheme 4 (FIG. 4), as follows:

(a) Preparation of 1-(2-Hydroxy-4,6-dimethylphenyl) ethanone (25): TiCl$_4$ (1.2 mL, 11 mmol) was added slowly to 3,5-dimethylphenol 24 (10mmol, 1.22 g) placed in a flask flushed with argon at room temperature. The resulting dark cherry-colored mixture was stirred at room temperature, and when gas evolution ceased, acetyl chloride (15 mmol, 1.1 mL) was added to the solid. The resulting thick solution was stirred at room temperature for 15 minutes, then brought to 120° C. and left to stir at this temperature for an additional hour. The reaction mixture was then cooled to room temperature, diluted with methylene chloride (30 mL) and quenched with H$_2$O (30 mL). The organic layer was washed with H$_2$O (2×30 mL), dried (Na$_2$SO$_4$), and concentrated under reduced pressure. The crude material was purified by silica gel column chromatography using a mixture of 5% of ethyl acetate in hexanes to yield 1.38 g of a white solid (84% yield). mp 58–60° C.; $^1$H NMR (CDCl$_3$) δ 2.27 (s, 3H, CH$_3$), 2.56 (s, 3H, CH$_3$), 2.63 (s, 3H, COCH$_3$), 6.54 (s, 1H, Ar—H), 6.65 (s, 1H, Ar—H), 12.64 (s, 1H, OH); $^{13}$C NMR (CDCl$_3$) δ 21.77, 24.87, 33.47, 116.94, 119.31, 124.70, 139.65, 146.32, 163.79, 205.64; IR (KBr, ν cm$^{-1}$) 2927, 1622, 1353, 1216; MS (ESI) 165 (M+1). Anal. Calcd for C$_{10}$H$_{12}$O$_2$: C, 73.15, H, 7.37. Found: C, 73.33, H, 7.37.

(b) Preparation of (2E)-1-(2-hydroxy-4,6-dimethylphenyl)-3-(3,4,5-tribenzyloxyphenyl) prop-2-en-1-one (26): The chalcone 26 was synthesized from the acetophenone 25 and benzaldehyde 12 using NaH/DMF, using the same procedure as for chalcone 19 (Scheme 3). The chalcone 26 was isolated as a yellow solid in 79% yield. $^1$H NMR (300 MHz, CDCl$_3$): δ 2.30 (s, 3H, CH$_3$), 2.45 (s, 3H, CH$_3$), 5.13 (s, 2H, OCH$_2$Ph), 5.14 (s, 4H, OCH$_2$Ph), 6.59 (s, 1H, 8-H), 6.67 (s, 1H, 6-H), 6.84 (s, 2H, 2',6'-H), 7.00 (d, J=16.0 Hz, 1H, CH═CH), 7.25–7.42 (m, 15 H, Ar—H), 7.55 (d, J=16.0 Hz, 1H, CH═CH), 11.24 (s, 1H, OH). $^{13}$C NMR (CDCl$_3$): δ 21.87, 23.62, 71.62, 75.55, 108.67, 116.10, 120.88, 124.37, 126.61, 127.57, 128.22, 128.28, 128.46, 128.79, 128.84, 130.42, 136.97, 137.71, 138.44, 141.20, 143.40, 145.50, 153.31, 161.81, 196.13.

(c) Preparation of 5,7-dimethyl-2-(3,4,5-tribenzyloxyphenyl)-2H-chromene (27): To a solution of chalcone 26 (535 mg, 0.94 mmol) in a mixture of tetrahydrofuran/methanol (5 mL/20 mL) was added sodium borohydride (49 mg, 1.3 mmol). The solution was brought to reflux (60–67° C.) and maintained at this temperature for 18 hours after which all starting material was consumed and a polar material was formed which was found to be the very unstable allylic alcohol (from chalcone reduction). The reaction mixture was cooled and the solvent was evaporated under reduced pressure. The residue was diluted with ethyl acetate and water. Evaporation of the dried organic layer yielded a viscous oil, which was subsequently dissolved in 5 mL of ethyl acetate. To this solution, a catalytic amount of boron trifluoride etherate (10 mol %) was added at room temperature. The mixture was left to stir overnight at the same temperature until complete cyclization giving the desired flavene 27 in 53% yield as a white solid after evaporation of solvent and flash chromatography of the crude material using methylene chloride. $^1$H NMR (300 MHz, CDCl$_3$): δ 2.24 (s, 3H, CH$_3$), 2.29 (s, 3H CH$_3$), 5.02 (s, 2H, OCH$_2$Ph), 5.08 (s, 4H, OCH$_2$Ph), 5.68–5.72 (m, 2H,), 6.49 (s, 1H, 8-H), 6.56 (s, 1H, 6-H), 6.68 (dd, J=2.7, 11.1 Hz, 1H, 3-H), 6.77 (s, 2H, 2', 6'-H), 7.28–7.41 (m, 15H, Ar—H).

(d) Preparation of (2,3-trans)-5,7-dimethyl-2-(3,4,5-tribenzyloxyphenyl)chroman-3-ol (28): The flavanol 28 was synthesized by the same hydroboration/oxidation sequence as used for 6, yielding exclusively the 2,3-trans alcohol 28 as a white solid in 95% yield after silica gel chromatography with 30% of ethyl acetate in hexanes. $^1$H NMR (300 MHz, CDCl$_3$): δ 1.63 (d, J=3.6 Hz, 1H, OH), 2.21 (s, 3H, CH$_3$), 2.27 (s, 3H, CH$_3$), 2.64 (dd, J=9.0, 16.3 Hz, 1H, 4-H), 2.98 (dd, J=5.7, 16.3 Hz, 1H, 4-H), 3.95–4.06 (m, 1H, 3-H), 4.55 (d, J=8.4 Hz, 1H, 1H, 2-H), 5.05–5.15 (m, 6H, OCH$_2$Ph), 6.63 (s, 1H, 8-H), 6.65 (s, 1H, 6-H), 6.74 (s, 2H, 2', 6'-H), 7.24–7.44 (m, 15H, Ar—H).

(e) Preparation of SR 13911: A 5 mL thick wall microwave vial (Personal Chemistry, Inc.) was charged with 28 (400 mg, 0.7 mmol), 3,4,5-tribenzyloxybenzoic acid (616 mg, 1.4 mmol), BOP reagent (1.24 g, 2.8 mmol), DMAP (342 mg, 2.8 mmol), diisopropylethylamine (610 μL, 3.5 nmmol) and 1 mL of freshly distilled DMF. The vial was sealed and heated in a single mode (MW) Smith Creator™ chamber for 5 minutes at 170° C., after which all starting material was consumed as shown by TLC. The mixture was diluted with ethyl acetate and 1M solution of HCl. After work up, the crude material was purified by flash chromatography on silica gel with 20% of ethyl acetate in hexanes to yield 640 mg of hexabenzyloxy-protected SR 13911 as a white solid (92% yield). $^1$H NMR (300 MHz, CDCl$_3$): δ 2.18 (s, 3H, CH$_3$), 2.30 (s, 3H, CH$_3$), 2.77 (dd, J=7.0, 16.3 Hz, 1H, OH), 2.99 (dd, J=5.4, 16.3 Hz, 1H, OH), 4.97–5.20 (m, 13H, OCH$_2$Ph, 3-H), 5.42–5.48 (m, 1H, 2-H), 6.67 (s, 1H, 8-H), 6.69 (s, 1H, 6-H), 6.72 (s, 2H, 2', 6'-H), 7.18–7.46 (m, 31H, Ar—H, 2", 6"-H), 7.68 (s, 1H, 2", 6"-H).

This compound was then dissolved in 1,4-dioxane and treated with 100 mg of Pd/C. The mixture was allowed to stir at room temperature under 1 atm of H$_2$ for 15–18 h. The suspension was then filtered, the solvent was evaporated and the residue was chromatographed on silica gel using 10% of methanol in methylene chloride to provide 165 mg of SR 13911 as a white solid (60% yield). $^1$H NMR (300 MHz, acetone-d$_6$): δ 2.15 (s, 3H, CH$_3$), 2.24 (s, 3H, CH$_3$), 2.78 (dd, J=6.3, 17.1 Hz, 1H, 4-H), 2.91 (dd, J=5.4, 17.1 Hz, 1H, 4-H), 5.10 (d, J=6 Hz, 1H, 2-H), 5.43 (q, J=5.4 Hz, 1H, 3-H), 6.47 (s, 2H, 2', 6'-H), 6.59 (s, 1H, 8-H), 6.60 (s, 1H, 6-H), 7.03 (s, 2H, 2", 6"-H ), 8.00 (br, exchangeable OHs).

EXAMPLE 9

Synthesis of cis-5,7-dimethyl-2-(3,4,5-trihydroxy-phenyl)-3,4-dihydro-2H-chroman-3-yl, 3,4,5-trihydroxy-benzoic acid ester (SR 13912)

SR 13912:

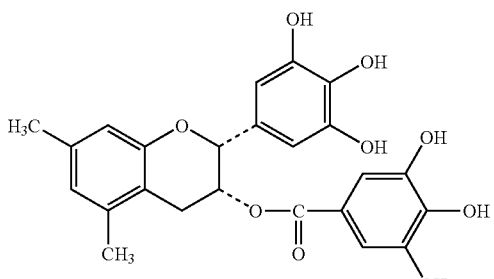

The above compound, also an A-ring analog of EGCG, was synthesized according to Scheme 4 (FIG. 4), as follows:

(a) Preparation of 5,7-dimethyl-2-(3,4,5-tribenzyloxyphenyl)-2H-chromen-3(4H)-one (29): 3-Flavanone 29 was prepared using the Dess-Martin periodinane oxidation procedure used for the synthesis of 7. The white crystalline 3-flavanone 29 was obtained in 80% yield after flash chromatography on silica gel using 10% of ethyl acetate in hexanes. $^1$H NMR (300 MHz, CDCl$_3$): δ 2.18 (s, 3H, CH$_3$), 2.31 (s, 3H, CH$_3$), 3.43 (d, J=19.9 Hz, 1H, 4-H), 3.52 (d, J=19.9 Hz, 1H, 4-H), 5.00 (m, 6H, OCH$_2$Ph), 5.20 (s, 1H, 2-H), 6.69 (s, 2H, 2', 6'-H), 6.74 (s, 1H, 8-H), 6.77 (s, 1H, 6-H), 7.24–7.41 (m, 15H, Ar—H). $^{13}$C NMR (300 MHz, CDCl$_3$): δ 18.96, 21.33, 37.09, 71.41, 75.40, 82.93, 106.47, 116.13, 116.52, 125.60, 127.71, 127.99, 128.10, 128.36, 128.69, 130.73, 136.90, 137.14, 138.04, 138.22, 138.80, 153.15, 153.43, 205.63.

(b) Preparation of (2,3-Cis)-5,7-dimethyl-2-(3,4,5-tribenzyloxyphenyl)chroman-3-ol (30): The cis 3-flavanol 30 was synthesized by the stereoselective L-selectride reduction of the 3-flavanone 29 in the same manner as given for 3-flavanol 23 (Scheme 3). The final product was obtained as a colorless oil (62% yield), after flash chromatography on silica gel using 20% of ethyl acetate in hexanes. $^1$H NMR (300 MHz, CDCl$_3$): δ 1.73 (s, 1H, OH), 2.20 (s, 3H, CH$_3$), 2.27 (s, 3H, CH$_3$), 2.83 (d, J=17.1 Hz, 1H, 4-H), 2.95 (dd, J=4.2, 17.1 Hz, 1H, 4-H), 4.23–4.28 (m, 1H, 3-H), 4.87 (s, 1H, 2-H), 5.06 (s, 2H, OCH$_2$Ph), 5.13 (s, 4H, OCH$_2$Ph), 6.66 (s, 1H, 8-H), 6.68 (s, 1H, 6-H), 6.81 (s, 2H, 2', 6'-H), 7.25–7.43 (m, 15H, Ar—H). MS (ESI, positive ion) 595 (M+Na), 1167 (2M+Na).

(c) Preparation of SR 13912: SR 13912 was synthesized using exactly the same procedure as described in Example 8 for SR 13911. The hexabenzyloxy-protected SR 13912 was obtained in 57% yield as colorless viscous oil after flash chromatography using 20% ethyl acetate in hexanes. $^1$H NMR (300 MHz, CDCl$_3$): δ 2.21 (s 3H, CH$_3$), 2.31 (s, 3H, CH$_3$), 2.93 (d, J=17.7 Hz, 1H, 4-H), 3.15 (dd, J=4.5, 17.7 Hz, 1H, 4-H), 4.71 (d, J=11.4 Hz, 2H), 4.83 (d, J=11.4 Hz, 2H), 4.91 (s, 2H), 4.96 (s, 1H), 4.97 (s, 1H), 5.01 (s, 4H), 5.03 (s, 1H), 5.58–5.78 (m, 1H, 2-H), 6.70 (s, 1H), 6.75 (s, 2H), 6.79 (s, 1H), 7.19–7.34 (m, 32H, Ar—H).

Hydrogenolysis of this intermediate, as described above, provided the desired SR 13912 as a white solid in 53% yield. $^1$H NMR (300 MHz, acetone-d$_6$): δ 2.15 (s 3H, CH$_3$), 2.24 (s 3H, CH$_3$), 2.78 (d, J=17.8 Hz, 1H, 4-H), 3.17 (dd, J=5.1, 17.8 Hz, 1H, 4-H), 5.06 (s, 1H), 5.60–5.63 (m, 1H, 2-H), 6.60 (s, 1H, 8-H), 6.61 (s, 1H, 6-H), 6.63 (s, 2H, 2', 6'-H), 7.00 (s, 2H, 2",6"-H), 7.20 (br, exchangeable OH), 7.70 (br, exchangeable OH), 8.19 (br, exchangeable OH).

EXAMPLE 10

Synthesis of cis-5,7-dimethyl-2-(3,4,5-trihydroxy-phenyl)-3,4-dihydro-2H-chroman-3-yl, 4-Hydroxy-3,5-dimethyl-benzoic acid ester (SR 13913)

SR 13913:

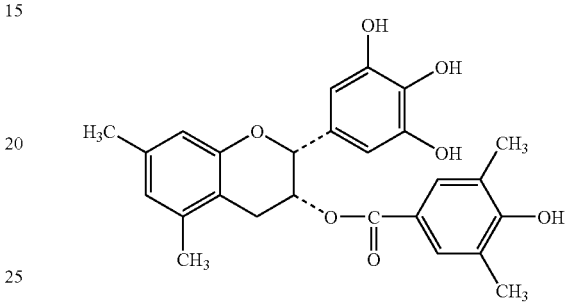

The above compound, an A- and D-ring analog of EGCG, was synthesized according to Scheme 4 (FIG. 4), using exactly the same procedure as described in Example 8 for SR 13911. The tetrabenzyloxy-protected SR 13913 was obtained in 83% yield as colorless viscous oil after flash chromatography using 20% ethyl acetate in hexanes. $^1$H NMR (300 MHz, CDCl$_3$): δ 2.21 (s 3H, CH$_3$), 2.22 (s, 6H, CH$_3$), 2.31 (s 3H, CH$_3$), 2.97 (d, J=17.4, 1H, 4-H), 3.15 (dd, J=4.8, 17.4 Hz, 1H, 4-H), 4.60 (s, 1H), 4.62 (s, 1H), 4.83 (d, J=11.7 Hz, 2H), 4.93 (s, 1H), 4.98 (s, 1H), 4.99 (d, J=11.7 Hz, 2H), 5.04 (s, 1H, 2-H), 5.48–5.78 (m, 1H, 3-H), 6.67 (s, 1H), 6.83 (s, 2H), 7.18–7.67 (m, 22H, Ar—H).

Hydrogenolysis of this intermediate gave the desired SR 13913 as a white solid in 60% yield. $^1$H NMR (300 MHz, acetone-d$_6$): δ 2.15 (s 3H, CH$_3$), 2.20 (s, 6H, CH$_3$), 2.24 (s 3H, CH$_3$), 2.90 (d, J=17.4 Hz, 1H, 4-H), 3.17 (dd, J=4.8, 17.4 Hz, 1H, 4-H), 5.10 (s, 1H), 4.00–4.05 (m, 1H, 3-H), 4.05 (s, 1H, 2-H), 5.09 (s, 1H,), 5.10 (s, 2H), 5.96 (s, 2H), 6.11–6.42 (br, exchangeable OH).

EXAMPLE 11

In vitro determination of growth inhibitory activity

Additional compounds according to the structures described above for compounds SR 13915, SR13916, SR13917, SR13918, SR13919, SR13920 and SR13921 were prepared according to the methods of Examples 1–10.

EXAMPLE 12

In vitro determination of growth inhibitory activity

Compounds of the invention were tested for their ability to inhibit growth in two breast cancer cell lines, MCF-7 (ER+) and MDA-MB-231 (ER−).

The growth inhibition assays were conducted using routine methods. Briefly, the cells were seeded in 24-well plates at a density of 2000 cells per well in 200 μL of water containing growth medium. To each well was added 10 μL of DMSO containing the dissolved test compound; final DMSO concentration in each well was not more than 0.5%. Each test compound was assayed at concentrations of 0.4, 2, 10, and 50 μM. The plates were incubated for eight days, with the media and test solutions replaced every third day. On Day 8, the viable cells were measured by the MTT assay, as described in Mosmann et al. (1983), "Rapid Colorimetric Assay for Cellular Growth and Survival: Application to Proliferation and Cytotoxicity," *J. Immunol. Method.* 65:55–63. The optical density at 575 nm of each test well was measured and compared to that for control wells, and the data used to calculate the percentage of growth inhibition at different concentrations. The $IC_{50}$ value (the concentration of growth inhibitor that results in 50% growth inhibition of the cells in culture relative to control cells not exposed to any growth inhibitor) was determined by plotting dose-response curves.

The calculated $IC_{50}$ values are set forth in Table 1, with the results representing the average of at least two experiments conducted for each compound at each of the four concentrations. As may be seen, a number of the experimental compounds demonstrated growth inhibitory activity against both of the breast cancer cell lines.

TABLE 1

| Compound | Growth Inhibition ($IC_{50}$) (μM) | |
|---|---|---|
| | MCF-7 (ER+) | MDA-MB-231 (ER−) |
| SR 13194 | >100 | >100 |
| SR 13195 | >100 | >100 |
| SR 13196 | 8.39 | 19.63 |
| EGCG (2,3-cis) | 8.22 | 11.94 |
| EGC (2,3-cis) | 29.75 | 27.26 |

The foregoing procedures were repeated with additional compounds of the invention to evaluate the their ability to inhibit growth in MCF-7 (ER+) and MDA-MB-231 (ER−). The results-obtained are set forth in Table 2:

TABLE 2

| Compound | Growth Inhibition ($IC_{50}$) (μM) | |
|---|---|---|
| | MCF-7 (ER+) | MDA-MB-231 (ER−) |
| SR 13911 | 23.56 | 25.68 |
| SR 13912 | 21.8 | 53.68 |
| SR 13913 | 17.21 | 19.86 |
| SR 13915 | >100 | >100 |
| SR 13916 | 6.61 | 10.16 |
| SR 13917 | 6.12 | 2.98 |
| SR 13918 | >100 | 46.76 |
| SR 13919 | 8.35 | 7.76 |
| SR 13920 | 33.09 | 9.97 |
| SR 13921 | | |
| SR 13197 | >100 | >100 |
| SR 13198 | 42.06 | 35.85 |
| SR 13199 | na | na |
| SR 13200 | 22.90 | 22.58 |
| EGCG | 37.1 | 36.85 |

EXAMPLE 13

IN VITRO DETERMINATION OF GROWTH INHIBITORY ACTIVITY

An anchorage-independent growth inhibition assay was performed as described in Korytynski, et al. (1996) "The development of an anchorage-independence assay using human lung tumor cells to screen potential chemopreventive agents," *Anticancer Res.* 16, 1091–1094; and Sharma, et al. (1997) "The anchorage-independent assay as a screening tool to identify potential chemopreventive agents," *Methods Cell Sci.* 19, 9–12. The assay measures the inhibition of colony formation of human lung tumor cells (A427) cells grown in soft agar. In this assay, A427 cells were grown in the presence of the test agent, SR 13196, EGCG or 13-cis-RA Control samples were tested using an equivalent volume of DMSO alone. A concurrent assay for cell survival was also performed.

As can be seen from the data presented in the table below, SR 13196 inhibited colony formation to a much greater extent than either EGCG or 13-cis-RA At the highest concentration of SR 13196 tested (25 μM), 81% inhibition of the growth of the tumor cells was observed. In comparison, at the same concentration, EGCG and 13-cis-RA only inhibited 50% and 43% respectively. Similarly, at the highest concentration tested, SR 13196 showed only 11% surviving cells, in comparison and 68% for EGCG and 13-cis-RA respectively. Thus, SR 13196 inhibits colony formation of A427 cells in vitro, as well as their survival, and in a dose-dependent manner.

TABLE 3

| Compound | Dose (μM) | Surviving Fraction[a] | Observed Colonies | Expected Colonies[b] | % Inhibition[c] |
|---|---|---|---|---|---|
| DMSO Control | — | 1.0 | 390 | 390 | — |
| SR 13196 | 25 | 0.11 | 8 | 43 | 81 |
| | 12.5 | 0.12 | 28 | 52 | 46 |
| | 6.25 | 0.17 | 38 | 67 | 43 |
| | 3.12 | 0.41 | 108 | 160 | 32 |
| | 1.56 | 0.71 | 268 | 277 | 4 |
| EGCG | 25 | 0.39 | 97 | 191 | 50 |
| | 12.5 | 0.85 | 139 | 331 | 40 |
| | 6.25 | 0.97 | 282 | 378 | 25 |
| | 3.12 | 0.98 | 310 | 382 | 19 |
| | 1.56 | 0.99 | 398 | 386 | 0 |
| 13-cis-RA | 25 | 0.68 | 142 | 254 | 43 |
| | 12.5 | 0.74 | 179 | 265 | 35 |
| | 6.25 | 0.83 | 206 | 289 | 28 |
| | 3.12 | 0.82 | 269 | 320 | 16 |
| | 1.56 | 0.85 | 310 | 332 | 8 |

[a]Surviving Fraction = (Treated OD/Control OD);
[b]Expected Colonies = (Number of cells plated)(Surviving Fraction)(Frequency), where Frequency = Mean number of control colonies/2.5 × $10^4$;
[c]% Inhibition = Observed colonies/expected colonies.

Figure 5:
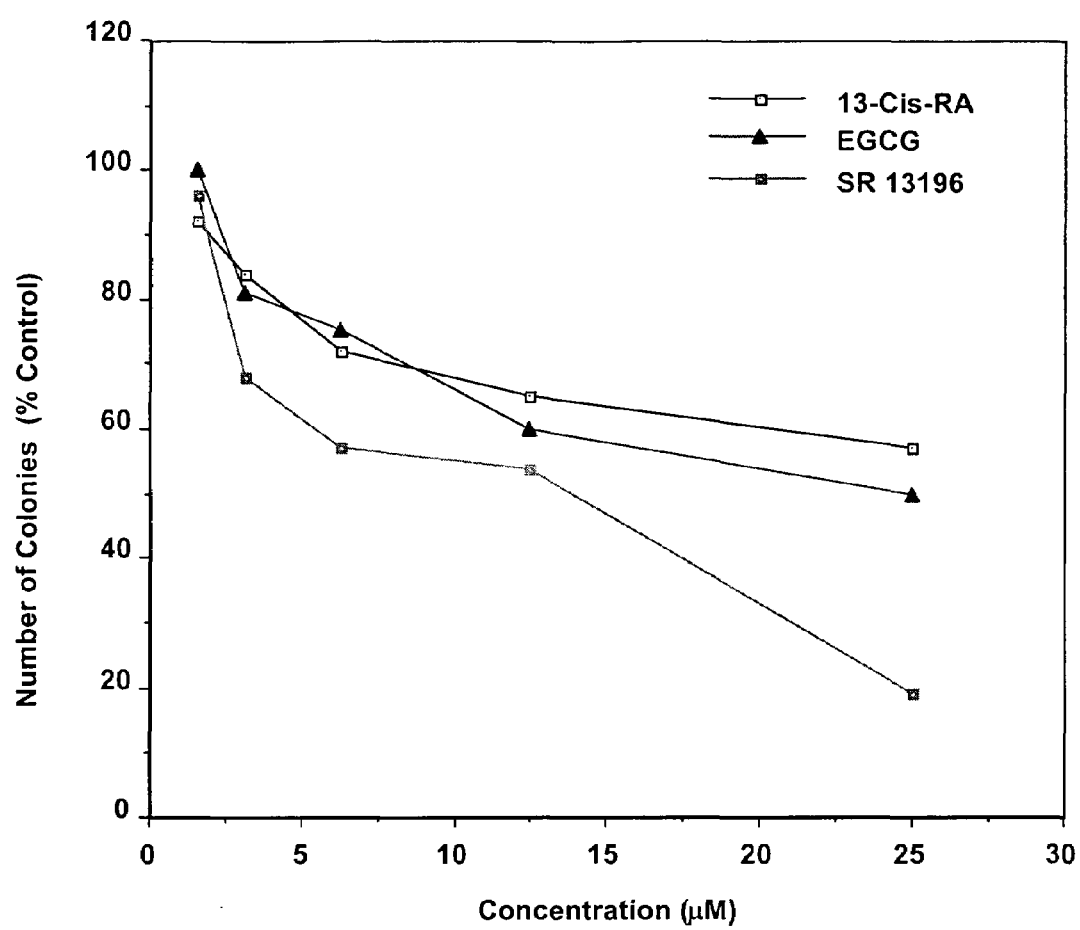
FIG. 5 depicts the inhibition of colony formation by SR 13196 and EGCG in the anchorage-independent cell growth inhibition assay in A427 human lung cancer cell line as described in Example 12.

FIG. 5 also graphically depicts the inhibition of colony formation by SR 13196 and EGCG in the anchorage-independent cell growth inhibition assay in A427 human lung cancer cell line as described in this Example.

EXAMPLE 14

IN VITRO DETERMINATION OF INTESTINAL ABSORPTION

Figure 6A:
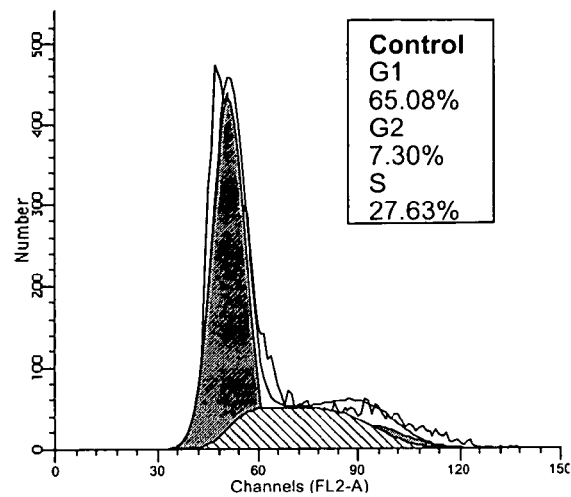
FIGS. 6A to 6C, collectively referred to as FIG. 6, depict cell cycle studies of ECGC and SR13196 of this invention in MCF-7 cells, as described in Example 14.
Figure 6B:
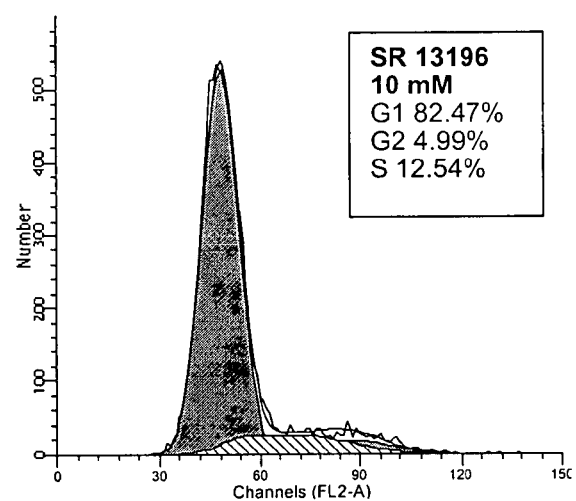
Figure 6C:
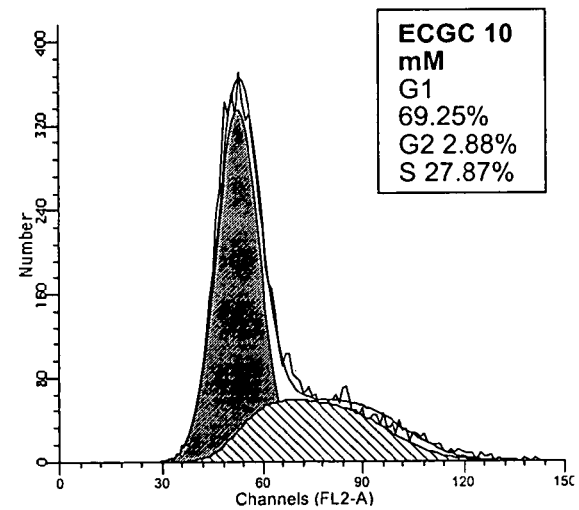

To establish that the analogs of EGCG also act via the same mechanisms as EGCG itself, the active analog SR 13196 in cell cycle studies in MCF-7 cells was examined. As shown in FIGS. 6A to 6C. SR 13196 at 10 μM (FIG. 6B), arrests the cell cycle in G1, similar to the effect of 10 μM of EGCG (FIG. 6C) but more pronounced.

EXAMPLE 15

In Vitro Determination of Intestinal Absorption

The Caco-2 human colon adenocarcinoma cell line has become accepted as a predictive model for human intestinal absorption. The advantage of using this in vitro model in conjunction with the earlier stages of drug design is that it saves a great deal of time and cost by avoiding the need for animal studies of uptake and bioavailability to pick the best preclinical candidate for further development. Results for the intestinal permeability of EGCG and the invention analogs in the Caco-2 model are shown in Table 2. Two commercially available radiolabelled standards, diazepam and ganciclovir, whose oral bioavailability is known, were used concurrently. The transport is reported as a permeability coefficient, P(app), which is compared to those of the known standards.

However, from experience with this Caco-2 model in this project, it appears that this model is somewhat difficult to work with on a routine basis. Furthermore, the results can be variable, depending on the recovery of the test compound from the basolateral well, during the assay. Inspite of these technical difficulties, EGCG consistently gave a low permeability coefficient (Papp), as seen in Table 2 below. Also, SR 13196 gave a higher Papp than EGCG itself, and some other compounds tested.

TABLE 4

| Experiment | Compound | $P_{app} \times 10^6$ (cm/sec) | % Absorbed (literature value) |
|---|---|---|---|
| 1 | EGCG | 2.41 ± 1.45 | |
|   | SR 13196 | 6.82 ± 0.83 | |
|   | Diazepam | 26.25 ± 3.11 | 100 |
|   | Ganciclovir | 1.97 ± 0.06 | 3 |
| 2 | EGCG | 0.90 ± 0.13 | |
|   | SR 13193 | Not detectable | |
|   | Diazepam | 28.19 ± 1.13 | 100 |
|   | Ganciclovir | 2.38 ± 1.00 | 3 |
| 3 | EGCG | 1.06 ± 0.43 | |
|   | SR 13911 | 1.42 ± 1.60 | |
|   | SR 13912 | not detectable | |
|   | SR 13913 | not detectable | |
| 4 | EGCG | 0.50 ± 0.20 | |
|   | SR 13913 | <0.06 | |
|   | SR 13915 | 5.17 ± 0.49 | |
|   | SR 13919 | <0.06 | |
|   | Diazepam | 22.9 ± 0.6 | 100 |
|   | Ganciclovir | 12.2 ± 2.9 | 3 |

<sup>a</sup>All drugs were used at a concentration of 100 μM. The experiments were run at pH 7.4.

What is claimed is:

1. A compound having the structural formula (I)

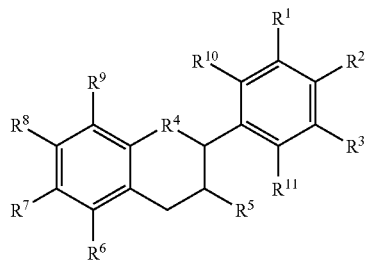

(I)

wherein:
$R^1$, $R^2$ and $R^3$ are selected from the group consisting of hydroxyl, alkyl, halo, sulfhydryl, alkoxy, and aryloxy;
$R^4$ is O;
$R^5$ is selected from the group consisting of SH, acyloxy, and $N(R^x)_2$ wherein the $R^x$ may be the same or different and are hydrogen or alkyl;
$R^6$ and $R^8$ are independently selected from the group consisting of hydroxyl, alkyl, alkoxy, and aryloxy;
$R^7$ and $R^9$ are independently selected from the group consisting of hydrogen, hydroxyl, alkyl, alkoxy, and aryloxy; and
$R^{10}$ and $R^{11}$ are independently selected from the group consisting of hydrogen, hydroxyl, alkyl, alkoxy, and halo,
with the proviso that when (a) $R^7$, $R^9$, $R^{10}$, and $R^{11}$ are hydrogen, and (b) $R^1$, $R^2$, $R^3$, $R^6$, and $R^8$ are hydroxyl, then (c) $R^5$ is other than 3,4,5-trihydroxybenzoyloxy or 3,4,5-trimethoxybenzoyloxy.

2. The compound of claim 1, wherein $R^1$, $R^2$ and $R^3$ are selected from the group consisting of hydroxyl, $C_1$–$C_6$ alkyl, halo, $C_1$–$C_6$ alkoxy, and $C_5$–$C_{12}$ aryloxy;
$R^5$ is selected from the group consisting of $C_6$–$C_{32}$ acyloxy and $NH_2$;
$R^6$ and $R^8$ are independently selected from the group consisting of hydroxyl, $C_1$–$C_6$ alkyl, $C_1$–$C_6$ alkoxy, and $C_5$–$C_{12}$ aryloxy;
$R^7$ and $R^9$ are independently selected from the group consisting of hydrogen, hydroxyl, $C_1$–$C_6$ alkyl, $C_1$–$C_6$ alkoxy, and $C_5$–$C_{12}$ aryloxy; and
$R^{10}$ and $R^{11}$ are independently selected from the group consisting of hydrogen, hydroxyl, $C_1$–$C_6$ alkyl, $C_1$–$C_6$ alkoxy, and halo.

3. The compound of claim 2, wherein $R^7$, $R^9$, $R^{10}$ and $R^{11}$ are hydrogen.

4. The compound of claim 3, in enantiomerically pure form in the 2β,3β-cis, 2α,3α-cis, 2α,3β-trans, or 2β,3α-trans configuration.

5. The compound of claim 3, comprising a racemic mixture of the 2α,3β-trans and 2β,3α-trans enantiomers.

6. The compound of claim 3, comprising a racemic mixture of the 2α,3α-cis and 2β,3β-cis enantiomers.

7. The compound of claim 3, wherein:
$R^5$ is an acyloxy substituent having the structure

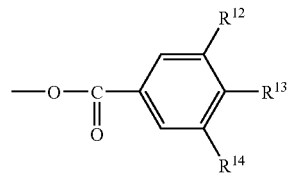

in which $R^{12}$, $R^{13}$, and $R^{14}$ are independently selected from the group consisting of hydrogen, hydroxyl, alkyl, alkoxy, and aryloxy.

8. The compound of claim 7, wherein:
$R^{12}$, $R^{13}$, and $R^{14}$ are selected from the groups consisting of hydroxyl, $C_1$–$C_6$ alkyl, $C_1$–$C_6$ alkoxy, and $C_5$–$C_{12}$ aryloxy.

9. The compound of claim 8, wherein:
$R^{12}$, $R^{13}$, and $R^{14}$ are independently selected from the group consisting of hydroxyl, methyl, and methoxy, and benzyloxy.

10. A compound having the structural formula (II)

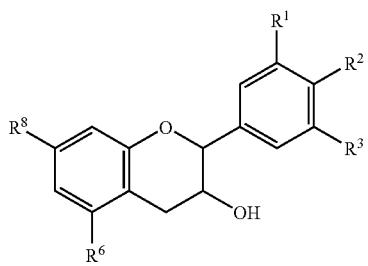

(II)

wherein:
$R^1$, $R^2$, and $R^3$ are selected from the group consisting of hydroxyl, alkyl, halo, sulfhydryl, alkoxy, and aryloxy; and
$R^6$ and $R^8$ are selected from the group consisting of alkyl, alkoxy, and aryloxy, wherein $R^1$, $R^2$, $R^3$, $R^6$ and $R^8$ are not all the same.

11. The compound of claim 10, wherein $R^1$, $R^2$ and $R^3$ are selected from the group consisting of hydroxyl, $C_1$–$C_6$ alkyl, halo, $C_1$–$C_6$ alkoxy, and $C_5$–$C_{12}$ aryloxy; and
$R^6$ and $R^8$ are selected from the group consisting of $C_1$–$C_6$ alkyl, $C_1$–$C_6$ alkoxy, and $C_5$–$C_{12}$ aryloxy.

12. The compound of claim 11, wherein $R^1$, $R^2$, and $R^3$ are independently selected from hydroxyl, methyl, and methoxy; and
$R^6$ and $R^8$ are independently selected from hydroxyl, methyl, and methoxy.

13. An analog of (−)-epigallocatechin-3-gallate (EGCG), wherein the analog contains at least one modification relative to ECGC that results in an $IC_{50}$ of less than 60 when the analog is evaluated for its ability to inhibit growth in a breast cancer cell line using MTT assay.

14. The analog of claim 13, wherein the analog contains at least one modification relative to ECGC that results in an $IC_{50}$ of less than 25 when the analog is evaluated for its ability to inhibit growth in a breast cancer cell line using MTT assay.

15. The analog of claim 14, wherein the analog contains at least one modification relative to ECGC that results in an $IC_{50}$ of less than 15 when the analog is evaluated for its ability to inhibit growth in a breast cancer cell line using MTT assay.

16. A compound having the structural formula selected from

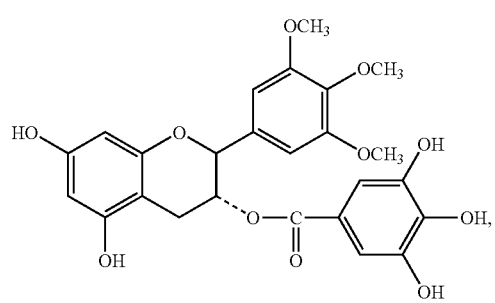

-continued

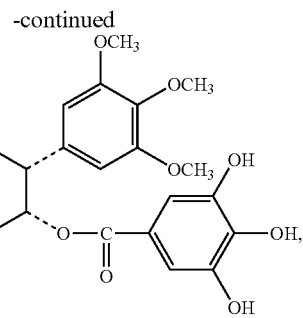

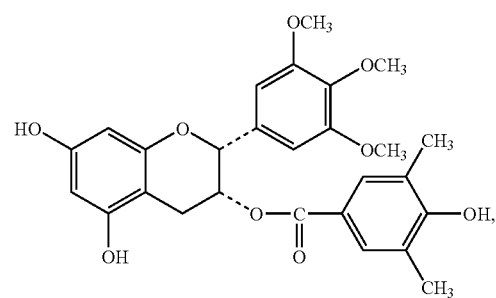

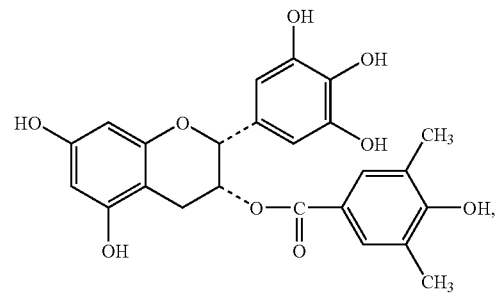

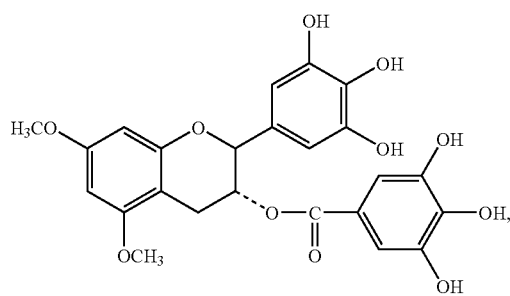

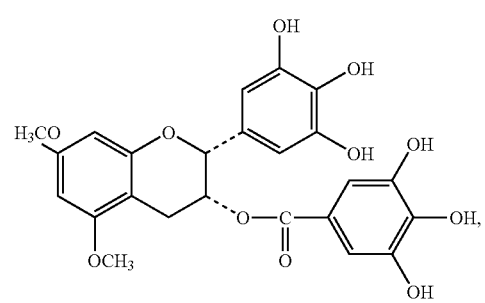

-continued

17. A pharmaceutical composition comprising a therapeutically effective amount of the compound of claim 1 in combination with a pharmaceutically acceptable carrier.

18. A pharmaceutical composition comprising a therapeutically effective amount of the compound of claim 2 in combination with a pharmaceutically acceptable carrier.

19. A pharmaceutical composition comprising a therapeutically effective amount of the compound of claim 3 in combination with a pharmaceutically acceptable carrier.

20. A pharmaceutical composition comprising a therapeutically effective amount of the compound of claim 4 in combination with a pharmaceutically acceptable carrier.

21. A pharmaceutical composition comprising a therapeutically effective amount of the compound of claim 5 in combination with a pharmaceutically acceptable carrier.

22. A pharmaceutical composition comprising a therapeutically effective amount of the compound of claim 7 in combination with a pharmaceutically acceptable carrier.

23. A pharmaceutical composition comprising a therapeutically effective amount of the compound of claim 8 in combination with a pharmaceutically acceptable carrier.

24. A pharmaceutical composition comprising a therapeutically effective amount of the compound of claim 14 in combination with a pharmaceutically acceptable carrier.

25. The composition of any one of claims 17 through 24, wherein the pharmaceutically acceptable carrier is suitable for oral administration and the composition comprises an oral dosage form.

26. The composition of claim 25, wherein the oral dosage form is a tablet.

27. The composition of claim 25, wherein the oral dosage form is a capsule.

28. The composition of any one of claims 17 through 24, wherein the pharmaceutically acceptable carrier is suitable for parenteral administration and the composition comprises a parenterally administrable formulation.

* * * * *